(12) United States Patent
Gagne

(10) Patent No.: US 11,666,508 B2
(45) Date of Patent: Jun. 6, 2023

(54) BIOPROCESS VESSELS WITH INTEGRATED PUMP

(71) Applicant: ALPHINITY USA, INC., Carson City, NV (US)

(72) Inventor: Michael C. Gagne, Carson City, NV (US)

(73) Assignee: ALPHINITY USA, INC., Carson City, NV (US)

( * ) Notice: Subject to any disclaimer, the term of this patent is extended or adjusted under 35 U.S.C. 154(b) by 0 days.

(21) Appl. No.: 17/720,241

(22) Filed: Apr. 13, 2022

(65) Prior Publication Data

US 2022/0233402 A1 Jul. 28, 2022

Related U.S. Application Data

(63) Continuation of application No. 16/480,070, filed as application No. PCT/US2018/015777 on Jan. 29, 2018, now Pat. No. 11,331,248.

(Continued)

(51) Int. Cl.
*C12M 1/00* (2006.01)
*A61J 1/10* (2006.01)
(Continued)

(52) U.S. Cl.
CPC .............. *A61J 1/10* (2013.01); *B01F 27/61* (2022.01); *B01F 27/71* (2022.01); *B01F 27/91* (2022.01);
(Continued)

(58) Field of Classification Search
CPC ...... C12M 23/14; C12M 27/02; C12M 29/00; C12M 29/10
See application file for complete search history.

(56) References Cited

U.S. PATENT DOCUMENTS

| 4,983,102 A | 1/1991 | Swain |
| 5,676,531 A | 10/1997 | Muscarella et al. |

(Continued)

FOREIGN PATENT DOCUMENTS

| CN | 1 435 482 | 8/2003 |
| CN | 1435482 A1 | 8/2003 |

(Continued)

OTHER PUBLICATIONS

Invitation to Respond to Written Opinion dated Jul. 1, 2022, from Singapore Patent Application No. 11201906632W, (7 pages).

(Continued)

*Primary Examiner* — Jonathan M Hurst
(74) *Attorney, Agent, or Firm* — Vista IP Law Group LLP

(57) ABSTRACT

A bioprocess vessel includes a flexible bag or substantially rigid container that defines an interior volume and having a bottom surface, the bottom surface being open or containing an aperture therein for the passage of fluid. A pump is secured to the bottom surface of the flexible bag or substantially rigid container. In some embodiments is secured directly to the flexible bag or substantially rigid container. In other embodiments, the pump is secured indirectly the flexible bag or substantially rigid container using, for example, a port that extends through the aperture on the bottom surface. The port or flanged surface may also be integrated into the pump, which is secured to the vessel. An optional mixing adaptor may be provided inside the interior volume of the flexible bag or substantially rigid container and at least partially covers the inlet that leads to the pump.

14 Claims, 25 Drawing Sheets

Related U.S. Application Data

(60) Provisional application No. 62/452,783, filed on Jan. 31, 2017.

(51) Int. Cl.

| | | |
|---|---|---|
| *C12M 3/00* | (2006.01) | |
| *C12M 1/06* | (2006.01) | |
| *F04D 1/00* | (2006.01) | |
| *F04D 29/40* | (2006.01) | |
| *B01F 27/61* | (2022.01) | |
| *B01F 27/71* | (2022.01) | |
| *B01F 27/91* | (2022.01) | |
| *B01F 35/513* | (2022.01) | |
| *B01F 35/75* | (2022.01) | |
| *A61J 1/14* | (2023.01) | |
| *F04B 43/06* | (2006.01) | |
| *B01F 101/44* | (2022.01) | |

(52) U.S. Cl.
CPC ........ *B01F 35/513* (2022.01); *B01F 35/7544* (2022.01); *C12M 23/14* (2013.01); *C12M 23/46* (2013.01); *C12M 27/02* (2013.01); *C12M 29/10* (2013.01); *F04D 1/00* (2013.01); *F04D 29/40* (2013.01); *A61J 1/1481* (2015.05); *B01F 2101/44* (2022.01); *F04B 43/06* (2013.01)

(56) References Cited

U.S. PATENT DOCUMENTS

| | | | |
|---|---|---|---|
| 5,836,482 | A | 11/1998 | Ophardt et al. |
| 6,455,524 | B1 | 9/2002 | Bozung et al. |
| 7,972,058 | B2 | 7/2011 | Furey |
| 2003/0143727 | A1 | 7/2003 | Chang |
| 2008/0279039 | A1 | 11/2008 | Furey |
| 2009/0130704 | A1 | 5/2009 | Gyure |
| 2011/0013473 | A1 | 1/2011 | Ludwig et al. |
| 2012/0130341 | A1 | 5/2012 | Whitley |
| 2013/0270165 | A1 | 10/2013 | Shevits |
| 2016/0200038 | A1 | 7/2016 | Gagne et al. |
| 2016/0245714 | A1 | 8/2016 | Gagne et al. |
| 2016/0258846 | A1 | 9/2016 | Kunnecke et al. |
| 2016/0263599 | A1 | 9/2016 | Barron |
| 2016/0327416 | A1 | 11/2016 | Gagne et al. |
| 2016/0369902 | A1 | 12/2016 | Gagne et al. |
| 2017/0322100 | A1 | 11/2017 | Gagne et al. |
| 2018/0003305 | A1 | 1/2018 | Gagne et al. |
| 2018/0136026 | A1 | 5/2018 | Gagne et al. |
| 2018/0252326 | A1 | 9/2018 | Gagne et al. |
| 2018/0274689 | A1 | 9/2018 | Gagne et al. |
| 2019/0101154 | A1 | 4/2019 | Gagne et al. |
| 2019/0120667 | A1 | 4/2019 | Gagne et al. |
| 2019/0178393 | A1 | 6/2019 | Gagne et al. |
| 2019/0178742 | A1 | 6/2019 | Gagne et al. |

FOREIGN PATENT DOCUMENTS

| | | |
|---|---|---|
| WO | WO 2009/118014 | 10/2009 |
| WO | WO 2016/120708 | 8/2019 |

OTHER PUBLICATIONS

Response to Written Opinion dated Oct. 17, 2022 from Singapore Patent Application No. 11201906632W, (9 pages).
PCT International Search Report for PCT/US2018/015777, Applicant: Alphinity, LLC, Form PCT/ISA/210 and 220, dated May 16, 2018 (5pages).
PCT Written Opinion of the International Search Authority for PCT/US2018/015777, Applicant: Alphinity, LLC, Form PCT/ISA/237, dated May 16, 2018 (5 pages).
Clincke, Marie-Francoise, Very High Density of CHO Cells in Perfusion by ATF or TFF in WAVE BioreactorTM. Part I. Effect of the Cell Density on the Process, Biotechnol. Prog., 2013, vol. 29, No. 3.
Brochure, Single-Use Simplicity, www.eppendorf.com/catalog, 2017, (6pages).
Muller, Christian et al., The Flexibility of Small-Scale Single-Use Bioreactor Solutions, BioPharm International, www.biopharminternational.com. Aug. 2016, pp. 18-22.
PCT International Preliminary Report on Patentability (Chapter I of the Patent Cooperation Treaty) for PCT/US2018/015777, Applicant: Alphinity, LLC., Form PCT/IB/326 and 373, dated Aug. 15, 2019 (7pages).
Communication regarding the extended European search report dated Jan. 16, 2020 in European Patent Application No. 18747897.9, (6pages).
Communication pursuant to Rules 70(2) and 70a(2) EPC dated Feb. 4, 2020 in European Patent Application No. 18747897.9, (1page).
Response to extended European search report dated Aug. 14, 2020 in European Patent Application No. EP18747897.9, (48 pages).
Office Action dated Jun. 8, 2021 for Taiwanese Patent Application 107103443, (8 pages).
Written Opinion dated Oct. 30, 2020 for Singapore Patent Application No. 11201906632, (6 pages).
Response to Written Opinion dated Mar. 30, 2021 from Singapore Patent Application No. 11201906632W, (10 pages).
Response to first Office Action dated Dec. 29, 2021 for Taiwanese Patent Application 107103443, (87 pages).
Notice of Preliminary Rejection dated Nov. 21, 2022 for Korean Patent Application No. 10-2019-7025228, (9 pages).
Response to Notice of Preliminary Rejection dated Jan. 20, 2023 for Korean Patent Application No. 10-2019-7025228, (40 pages).

BIOPROCESS VESSELS WITH INTEGRATED PUMP

RELATED APPLICATION

This Application is a continuation of U.S. application Ser. No. 16/480,070 filed on Jul. 23, 2019, now issued as U.S. Pat. No. 11,331,248, which is a U.S. National Stage filing under 35 U.S.C. § 371 of International Application No. PCT/US2018/015777, filed Jan. 29, 2018, which claims priority to U.S. Provisional Patent Application No. 62/452,783 filed on Jan. 31, 2017, which are hereby incorporated by reference. Priority is claimed pursuant to 35 U.S.C. §§ 119, 371 and any other applicable statute.

TECHNICAL FIELD

The field of the invention generally relates to fluid-based systems and processes used in the manufacture, production, or capture of products. More specifically, the invention pertains to bioprocess fluid containers, media and buffer bags, reactors, and fermentation units used in connection with pharmaceutical and biological applications or other hygienic process industries.

BACKGROUND

Many commercial products are produced using chemical as well as biological processes. Pharmaceuticals, for example, are produced in commercial quantities using scaled-up reactors and other equipment. So-called biologics are drugs or other compounds that are produced or isolated from living entities such as cells or tissue. Biologics can be composed of proteins, nucleic acids, biomolecules, or complex combinations of these substances. They may even include living entities such as cells. For example, in order to produce biologics on a commercial scale, sophisticated and expensive equipment is needed. In both pharmaceutical and biologics, for example, various processes need to occur before the final product is obtained. In the case of biologics, mammalian cells may be grown in a container such as a growth chamber, reactor, bag or the like and nutrients may need to be carefully modulated into the unit holding the cells.

Importantly, biologic products produced by living cells or other organisms may need to be filtered, extracted, concentrated, and ultimately collected from the growth container. Waste products produced by cells typically have to be removed on a controlled basis from the growth container. Typically, desired biologic products produced by cells and/or waste products are pumped out of the container where growth occurs using a separate pumping device that is located downstream with respect container containing the cells. This pumped fluid that is removed from the growth chamber is typically subject to downstream processing such as separation or filtration. Filtration is performed to separate or concentrate a fluid solution and in biotechnology and pharmaceutical manufacturing processes is critical for the successful and efficient production of drugs and other desirable products.

Various separation and filtration devices can be used to process the fluid pumped of the container unit where cell growths occurs. One common technique that is used to filter or separate components from the fluid is tangential flow filtration (TFF) where a filter or membrane is used to filter species contained in the fluid based on, for example, physical size. The flow is tangential to the membrane to reduce the accumulation of waste products, dead cells, and biofilm that tends to clog the filter membrane. Another separation technique utilizes acoustic wave separation (AWS) technology for cell harvesting and clarification. In contrast to methods like TFF, AWS does not achieve separation of cells using a physical barrier or filter, but with high-frequency resonant ultrasonic waves.

More recently, perfusion methods for growing cells have been developed. In the perfusion method, culture medium which is depleted of nutrients and contains waste products generated by the cells, is continuously removed from the cell culture and replaced with fresh culture media. The perfusion method enables one to achieve high concentrations of cells and permits the production process to run continuously unlike batch process. In perfusion methods, there still is a need to separate and/or filter the generated drugs and waste products from the continuously circulate cells. Perfusion methods, however, are known to have lower reliability because the cells are frequently damaged during the separation and/or filtration process which separates the medium from the cells. Various solutions have been proposed to address the known disadvantages of perfusion growth methods. U.S. Pat. No. 6,544,424 discloses a fluid filtration system that attempts to address the low reliability of perfusion methods. The system described in the '424 patent utilizes a hollow fiber module that is coupled at one end to a separate diaphragm pump. The pump is used to generate alternating flow across follow fibers or a filter screen.

A problem with solutions such as that disclosed in the '424 patent is that the separate pump located downstream of the vessel containing cells is connected to the vessel through various conduits and the hollow fiber module. When incorporating pumps into fluid pathways, there is a need to design such systems to avoid problems caused by cavitation, vacuum or pulsed flow condition. Cavitation and non-steady flow conditions tend to lyse the delicate mammalian cells that are used in these manufacturing processes. Pumping and vessel systems must therefore be designed to avoid these problems. Technically, this means that the pump and system must be designed such that the Net Positive Suction Head Available ($NPSH_A$) exceeds the Net Positive Suction Head Available Required ($NPSH_R$) to ensure the pump will operate without cavitation or other adverse flow conditions. Unfortunately, when pumps are placed downstream from the container like that disclosed in the '424 patent, this inevitably tends to produce cavitation, vacuum, and problematic flow conditions that tend to kill or disrupt cells.

In addition, in many cell growth systems like those discussed above, a flexible segment of tubing connects the cell-containing vessel to the pump and any associated filtration/separation devices. Unfortunately, this configuration as illustrated in FIG. 1 suffers from a problem in that due to upstream "negative" pumping pressure, the flexible tubing may collapse in on itself as seen in the inset of FIG. 1. This collapse of the tubing causes the inner surfaces of the tubing to contact one another and thereby prevents the further flow of fluid in the tubing. Even if the tubing does not fully close off, the presence of the tubing may lead to cavitation and other deleterious pulsatile flow conditions. For example, the irregular and often tortious paths of the tubing or conduit disrupts the fragile state of cells. These flow conditions may cause damage to the pump as well as disrupting and interfering with the cells contained in the fluid.

SUMMARY

In one embodiment, a fluid vessel for containing biological fluids includes a pump that is either directly or indirectly incorporated into the fluid vessel. In one embodiment, a hole or aperture is located in a bottom surface of the vessel that allows passage of fluid out (or into the vessel). The hole or aperture, in some embodiments, may actually encompass most or all of the bottom surface of the vessel, leaving a perimeter or circumferential surface to which the pump is adhered to. The pump is incorporated into the vessel at the location of the aperture or opening at the bottom of the vessel. In some embodiments, the pump is secured to the vessel through an intermediate component such as a port or flange that passes through the aperture and is secured to the vessel in a fluid tight arrangement (or manufactured in conjunction with the vessel). The pump is then secured to the flange. In another embodiment, the pump is directly secured to the vessel. For example, the pump head of the pump may be integrally formed with the vessel during the manufacturing process. Alternatively, in still another embodiment, the pump head may be secured to the vessel using one or more fasteners. The pump head may also be directly bonded to the vessel using thermal bonding, an adhesive, glue, weld, or the like In one embodiment, the fluid vessel is a substantially rigid container. For example, the vessel may take the form of a tub, vat, barrel, bottle, tank, flask, or other container suitable for holding liquids. The fluid vessel may be incorporated into processes, in some embodiments, where the vessel is used as a bioreactor or fermenter. The fluid vessel may be made of any number of materials including metals, polymers, glass, and the like. In one preferred embodiment, the vessel is formed from a polymer or resin material and is made as a single-use device. Likewise, one or more portions of the pump (e.g., pump head) that is directly or indirectly secured to the vessel may also be made from a polymer or resin material which facilitates integration or bonding of the pump to the vessel. In some embodiments, both the pump and vessel are made from same material. In other embodiments, the pump and vessel are made from different materials.

In another embodiment, the fluid vessel is flexible container such as a bag. The bag is typically made from polymer or resin material(s) and may have any number of shapes and sizes. The flexible bag may be formed from multiple layers. The bag includes a pump that is directly or indirectly secured to a bottom surface of the bag. The bag and attached or integrated pump may be carried in a trolley, dolly, cradle, cart, holder, or other support container to hold the bag and pump in the proper orientation. In some embodiments, both the pump and bag are made from the same material. In other embodiments, the pump and bag are made from different materials.

In one embodiment, regardless of whether the vessel is flexible or substantially rigid, the pump includes a separate motor that is used to power and operate the pump. For example, one preferred embodiment of the pump is a diaphragm pump because of the gentle nature of the flows produced during operation. A diaphragm pump or membrane pump operates as positive displacement pump that uses moving membrane in combination with valves to pump fluid. In one embodiment, the drive shaft of the motor may be used to drive a nutating disk or wobble plate to actuate the diaphragm membrane to drive fluid through the pump. Alternatively, servo motors or electronic/magnetic actuators may be used to sequentially actuate the diaphragm membrane to achieve a similar pumping action. The pump includes an inlet port that receives the incoming fluid that passes through the aperture in the vessel or the open vessel bottom and an outlet port through which the pumped fluid passes.

In one embodiment of the invention the vessel itself is made to be single use or disposable. In addition, one or more components of the pump may be made disposable. For example, the pump head which in some embodiments is integrally formed with the vessel may be disposable or contain disposable components. In other embodiments where the pump head is secured to the vessel, the pump head may also be formed from one or more components that are single use components. Alternatively, the vessel, pump, and any interface components between the two like a port or flange may be sterilizable for reuse. The motor or other drive mechanism that is used to power and operate the pump is typically reusable.

In one embodiment, a bioprocess vessel having an integrated pump is a flexible bag that incorporates a pump. The flexible bag defines an interior volume and having a bottom surface, the bottom surface containing an aperture therein for the passage of fluid. The bioprocess vessel includes a pump having an inlet and an outlet, the pump being secured to the bottom surface of the flexible bag whereby fluid passes from the interior volume of the flexible bag and into the inlet of the pump.

In another embodiment, a single-use bioprocess vessel having an integrated pump is disclosed. The single-use bioprocess vessel includes a substantially rigid container formed from a resin or polymer material defining an interior volume and having a bottom surface. The single-use bioprocess vessel includes a pump having an inlet and an outlet, the pump being secured to the bottom surface of the substantially rigid container whereby fluid passes from the interior volume of the substantially rigid container and into the inlet of the pump. The single-use bioprocess vessel may take the form of a bioreactor or a fermentation unit.

The vessels described herein may include an optional mixing adapter that is secured either to the vessel itself or to the pump. The mixing adapter at least partially covers a portion of the inlet to the pump. The mixing adapter may be used to prevent solids and other materials that are fed into the vessel from directly entering the inlet of the port prior to properly mixing with the fluid.

DETAILED DESCRIPTION OF THE ILLUSTRATED EMBODIMENTS

Figure 1:
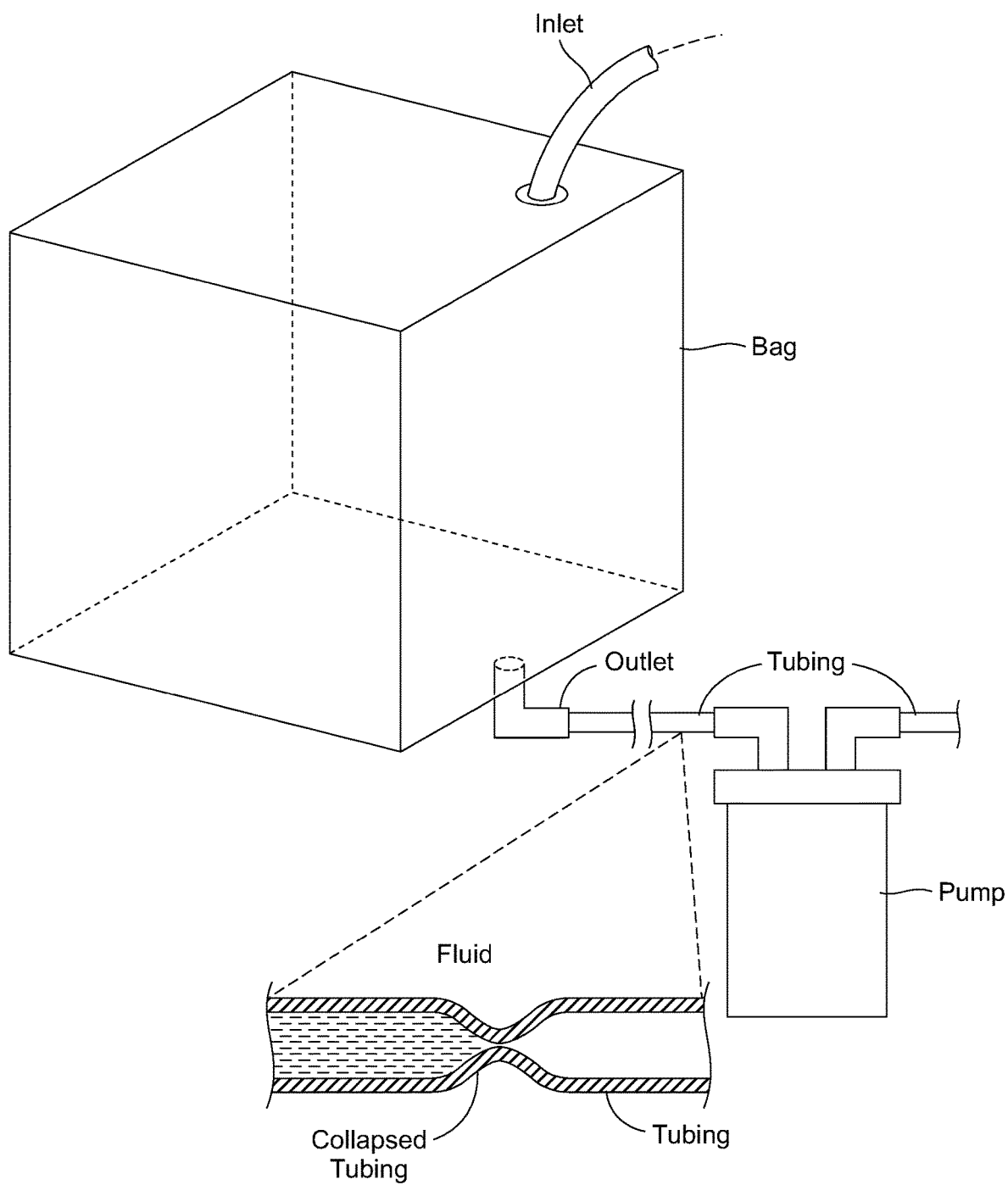
FIG. 1 illustrates a configuration of a bag and pump according to the prior art.

FIGS. 2A-2G illustrates one embodiment of a vessel 10 in the form of a flexible bag 12 that contains an integrated pump 14. The flexible bag 12 defines an interior volume that is used to hold fluids therein. The interior of the flexible bag 12 defines a sterile or aseptic environment in which fluid reagents or products are contained. The flexible bag 12 includes a number of side surfaces 16 as well as a top surface 18 and a bottom surface 20. The flexible bag 12 may have any number of shapes and sizes (e.g., one hundred liters or less to thousands of liters). The flexible bag 12 is illustrated in FIGS. 2A-2E has discrete surfaces (e.g., top, sides, bottom) although in some embodiments there need not be such discrete demarcations. The flexible bag 12 includes top surface 18 that, in some embodiments, may include one or more ports 22 that define access passageways to the interior of the flexible bag 12. The ports 22 may provide access for the addition of materials including solids, liquids, and gases. The port(s) 22 may also be used to sample fluid contained in the flexible bag 12. The ports 22 may also provide access for one or more probes or sensors that are used to monitor conditions within the interior of the flexible bag 12. The port 22 may also provide access for a mixer or agitation device. The ports 22 have any number of different sizes and configurations. While the ports 22 are illustrated being located in the top surface 18 the ports 22 may be located on any surface of the flexible bag 12. For example, a port 22 may be located at a side of the flexible bag 12 near the bottom surface 20 to provide access for a mixer device or the like.

The flexible bag 12 further includes a bottom or lower surface 20. The bottom surface 20 refers to the lowermost surface of the flexible bag 12 when oriented in the operational state. As explained herein, the fluid contained in the flexible bag 12 is pumped out of the flexible bag 12 at the bottom surface 20. This ensures that the fluid contained in the flexible bag always primes the pump 14. In addition, this ensures that all the fluid contained in the flexible bag 12 can be evacuated from the flexible bag 12 using the pump 14 (i.e., minimize or eliminate any dead volume in the system).

The flexible bag 12, in one embodiment, is made from one or more polymers or resin materials. For example, medical-grade resins compliant with class VI standards may be used. Additional examples include polyethylene (e.g., low density polyethylene (LDPE) or ultra-low density polyethylene (ULDPE) or polypropylene (PP), ethylene vinyl acetate (EFA), polyethylene terephthalate (PET), polyvinyl acetate (PVA), polyvinyl chloride (PVC), and the like are also contemplated. In some embodiments, the flexible bag 12 may by formed from multiple layers. For example, the inner layer that contacts the fluid may be made from LDPE. A second layer of polyvinyl acetate (PVA) or flexible polyvinyl chloride (PVC) may be used as an intermediate layer. An outer layer of LDPE or PET may provide mechanical strength. It should be appreciated that the integrated pump 14 embodiments described herein may be used with any number of different construction types, materials, and layers used for the flexible bag 12.

The pump 14 may be connected to the flexible bag 12 directly or indirectly as explained herein. A direct connection connects one or more surfaces of an inlet of the pump 14 to the flexible bag 12. In contrast, an indirect connection connects the pump 14 to the flexible bag 12 using a port 24. The embodiment illustrated in FIGS. 2A-2G utilizes a port 24. In either embodiment, there is no flexible conduit or tubing that is connected to the inlet of the pump 14 from the flexible bag 12. Instead, the inlet of the pump 14 is connected to the flexible bag 12 via the port 24 to interior of the flexible bag 12. In this regard, there is no concern with flexible tubing that collapses upon itself as illustrated in FIG. 1.

Figure 2A:
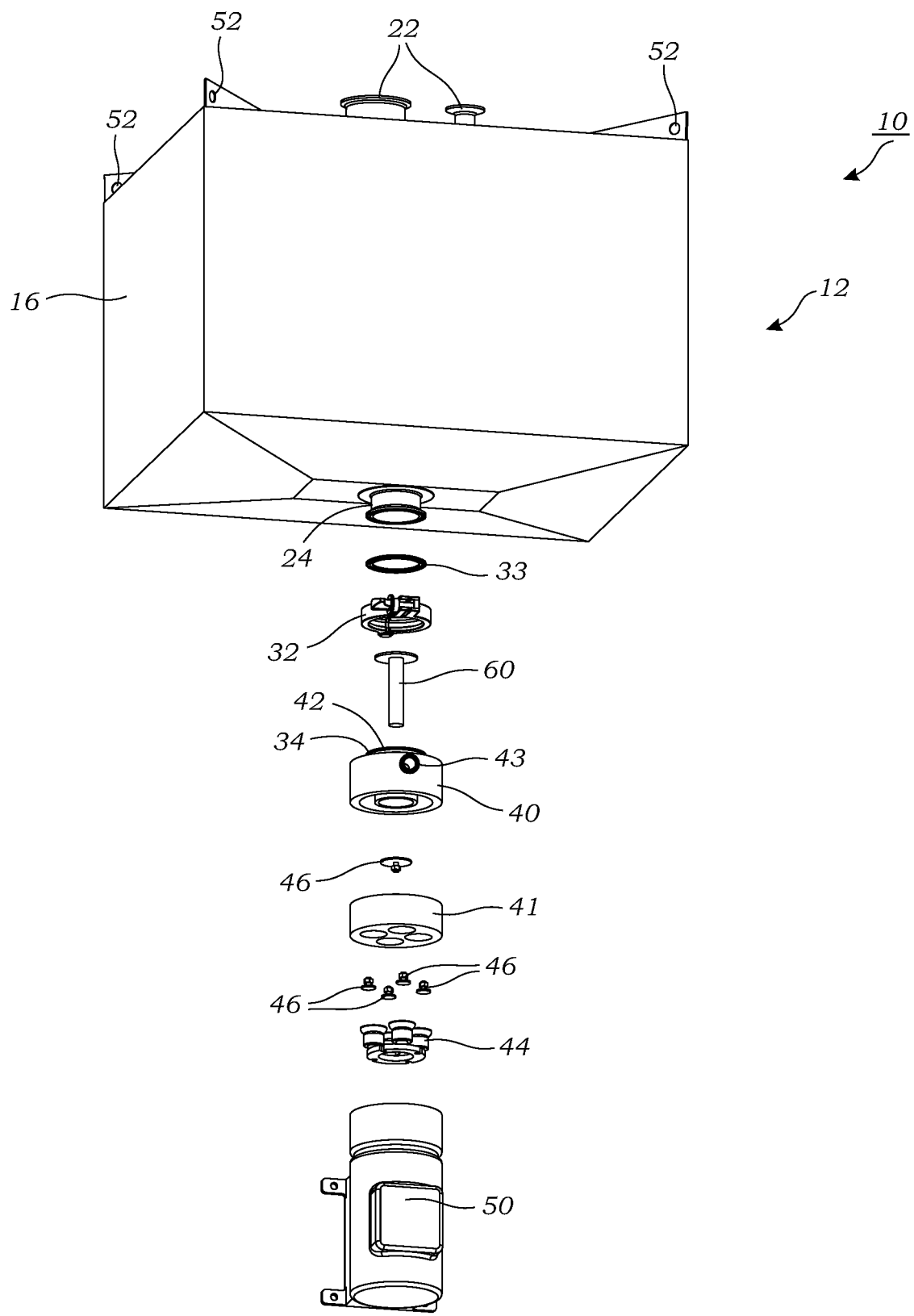
FIG. 2A illustrates an exploded view of a vessel in the form of a flexible bag that contains an integrated pump according to one embodiment.
Figure 2B:
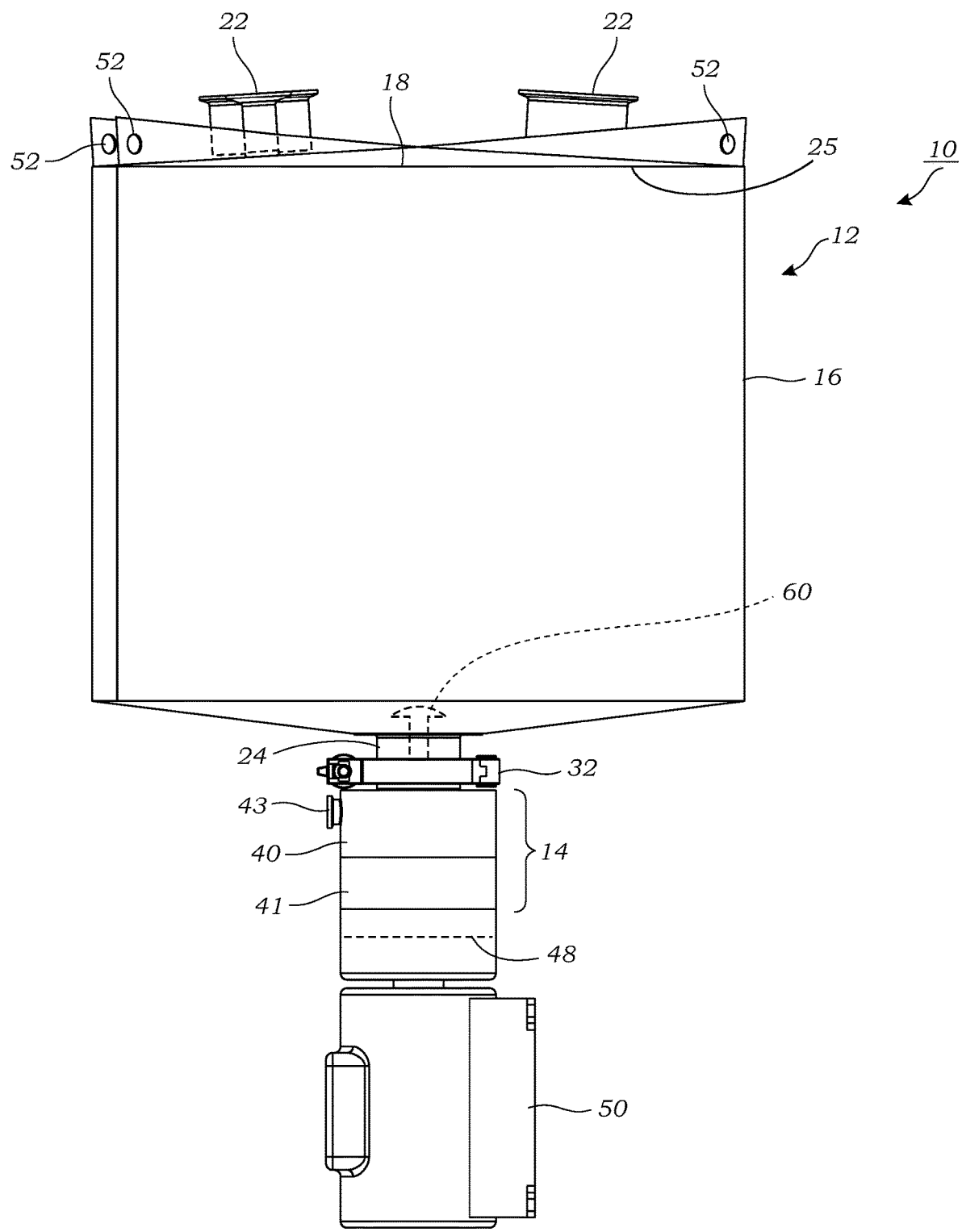
FIG. 2B illustrates a side view of the flexible bag with integrated pump of FIG. 2A.
Figure 2C:
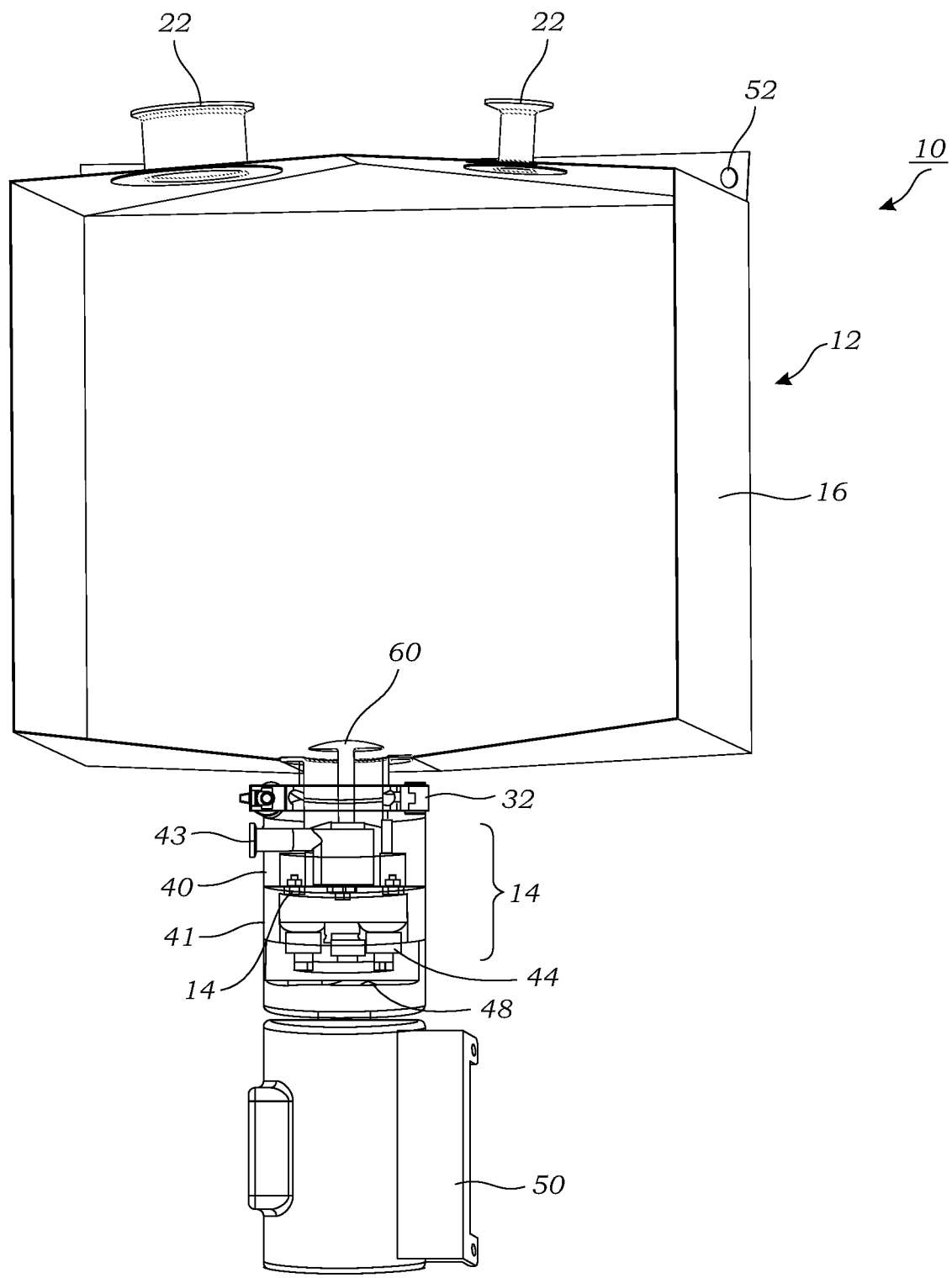
FIG. 2C illustrates a cross-sectional view of the flexible bag with integrated pump of FIG. 2A.
Figure 2D:
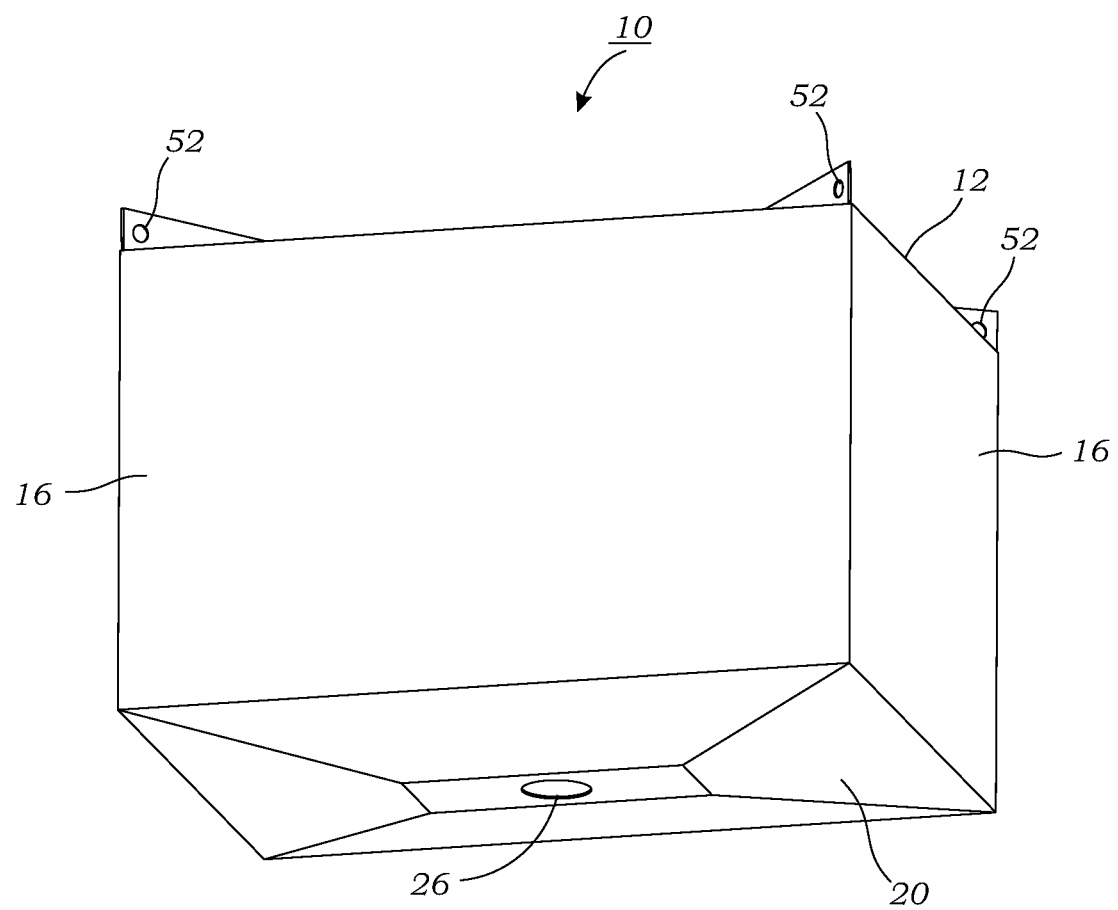
FIG. 2D illustrates a perspective view of a flexible bag illustrating the aperture formed in the bottom surface (no port is illustrated).
Figure 2E:
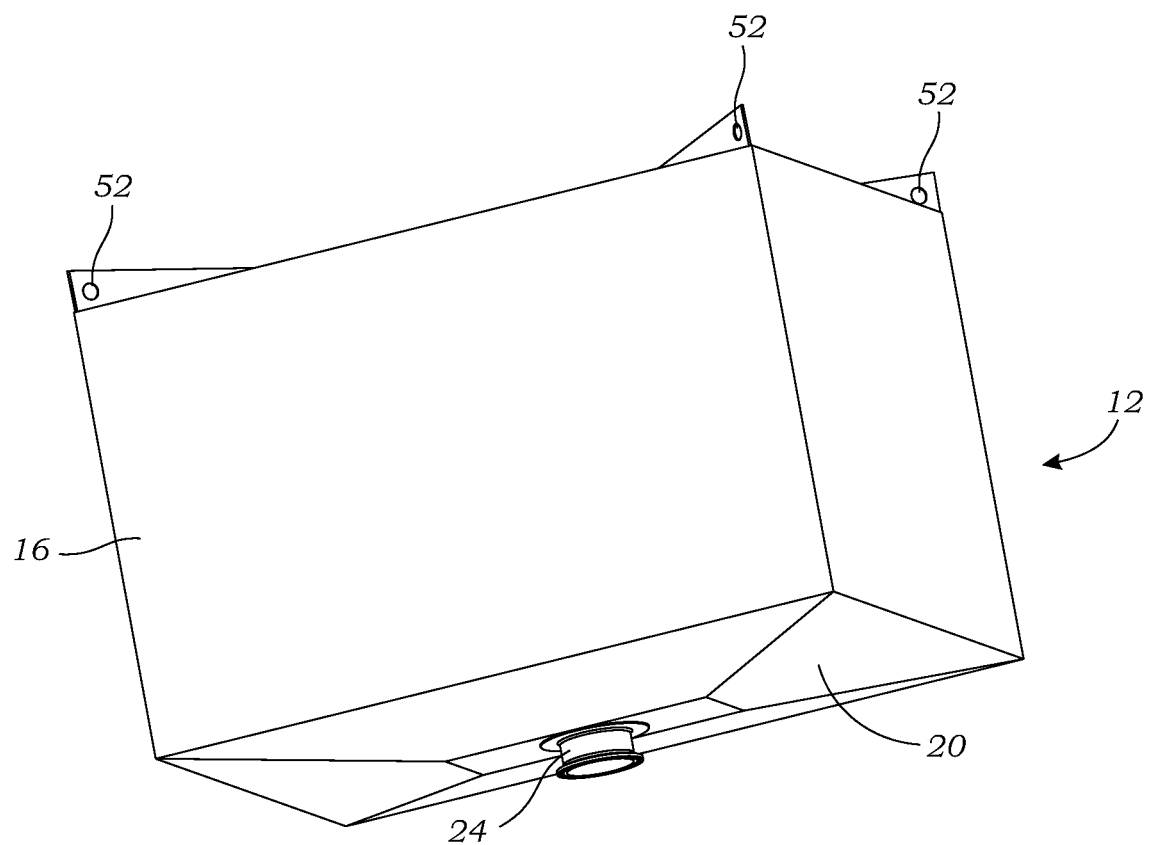
FIG. 2E illustrates a perspective view of a flexible bag illustrating the port disposed in the bottom surface of the flexible bag.

With reference to FIG. 2D, the flexible bag 12 includes an aperture 26 formed in the bottom surface 20 that permits the passage of fluid contained therein and serves as the inlet to the pump 14. Note that in this illustration the port 24 is removed to illustrate the aperture 26. The aperture 26 is typically circular in shape although other shapes are contemplated. The aperture 26 dimensions may vary depending upon the size of the flexible bag 12. FIG. 2E illustrates the flexible bag 12 with the port 24 disposed in the aperture.

Figure 2F:
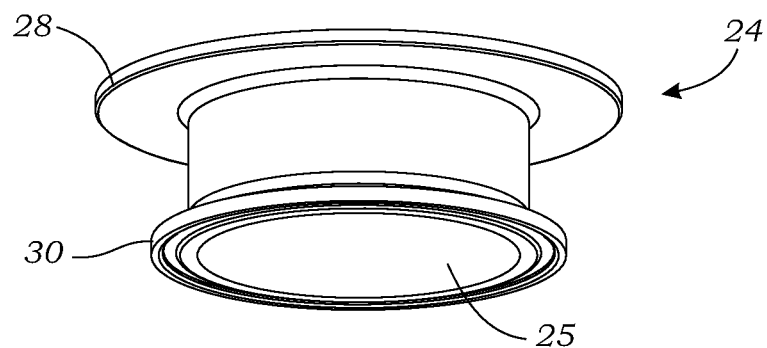
FIG. 2F illustrates a perspective view of a port that is disposed in the aperture of the flexible bag according to one embodiment. The port includes a flanged surface that is, in one embodiment, welded, bonded, or otherwise adhered to the flexible bag. The opposing end of the port has a connector end that is used to connect the pump.
Figure 2G:
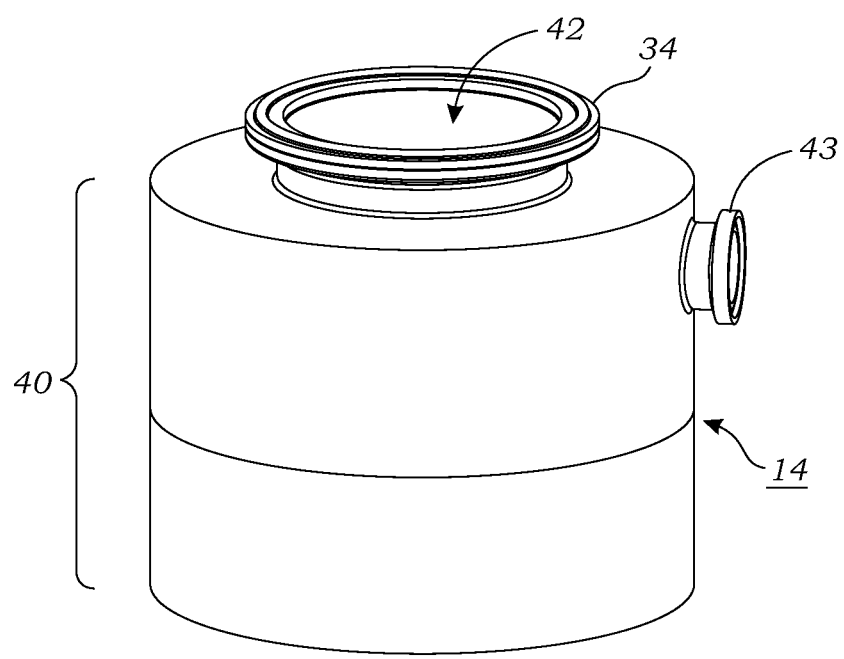
FIG. 2G illustrates one embodiment of a pump head.

In the embodiment illustrated in FIGS. 2A-2G, a port 24 is disposed inside the aperture 26 and is used as a connector to the pump 14 and also permits the passage of fluid contained in the flexible bag 12. FIG. 2F illustrates an isolated perspective view of the port 24. The port 24 includes a central aperture 25 that permits the passage of fluid through the port 24 and into the pump 14. The port 24 may be made from any number of materials including polymers materials such, for example, as polypropylene and polycarbonate, LDPE, high-density polyethylene (HDPE), or other medical-grade plastics or resins. The port 24 may even be formed from metal in some embodiments. In some embodiments, the port 24 is formed from the same material used for the flexible bag 12. In other embodiments, the port 24 is formed from a material that is different from the flexible bag 12. In the embodiment of FIGS. 2A-2G, the port 24 includes a first flanged surface 28 that is secured to the bottom surface 20 of the flexible bag 12. The first flanged surface 28 is secured to the bottom surface 20 of the flexible bag 12 in a fluid-tight seal. The first flanged surface 28 may be secured to an internal surface of the bottom surface 20 or an external surface of the bottom surface 20. Any number of ways of forming a fluid-tight seal with the bottom surface 20 may be used. For example, the first flanged surface 28 may be welded to the bottom surface 20 of the flexible bag 12. Any known method of welding such components together including heat welding, resistive welding, spin welding, friction welding, laser welding, and the like. An adhesive may also be used to secure the first flanged surface 28 to the bottom surface 20. Alternatively, the port 24 may be integrally formed with the flexible bag 12 during the manufacturing process (e.g., in the molding or formation of the flexible bag 12). The port 24 may also be made from a polymer or resin material than can bond the flexible bag 12 in response to, for example, applied heat.

The port 24 includes a second flanged surface 30 that is located on an opposing end of the port 24 and serves as a connector end to the port 24. The second flanged surface 30 is disposed outside the flexible bag 12 and is used as a connector to connect the pump 14. In one embodiment, the second flanged surface 30 is a tri-clamp (TC) type flanged surface 30 that is commonly used in bioprocess and pharmaceutical systems. In tri-clamp connections two mating flanged surfaces are connected to one another at an interface that typically contains a ferrule gasket 33 (seen in FIG. 2A) and a separate clamp 32 is used to secure the two components together. In the embodiment of FIGS. 2A-2G, the pump 14 includes corresponding connector end 34 that is secured to the second flanged surface 30 using the clamp 32. While the TC flanged surface 30 is illustrated it should be appreciated that other hygienic connectors such as male/female connectors, flange connectors, and the like (including proprietary connectors) may be used. Preferably, the port 24 does not extend far out of the flexible bag 12 (i.e., it should be as short as possible; yet still accommodate a clamp 32). Because the connector end 30 interfaces with a pump 14, these connections may typically be large, e.g., 6", 8", 10", or 12" diameter opening depending on the size of the pump 14; although other sizes are contemplated.

With reference to FIGS. 2A-2C and 2G, the pump 14 includes a pump head 40 and pump casing 41 that collectively contain the operating components of the pump 14. The pump head 40 includes an inlet 42 (FIGS. 2A and 2G) that is coupled to the flexible bag 12 by the connector end 34. Advantageously, the inlet 42 to the pump is directly connected to the flexible bag 12 via the connector end 34; there are no intervening tubes or conduits located between the pump 4 and the flexible bag 12. The outlet 43 of the pump 14 may terminate in a variety of ends or connectors used in biopharmaceutical processes. These include hygienic connectors, barb locks, hose barbs, flanges, TC connectors, disposable aseptic connectors (DAC), and the like. The outlet 43 may include or incorporate a valve directly or indirectly in the outlet 43. Tubing or other conduit may also interface directly with the outlet 43 of the pump 14 (e.g., by welding to the outlet 43 or the like). In still another embodiment, the outlet 43 of the pump 14 may simply be an aperture or opening through which fluid passes. This aperture or opening may be threaded internally so that the outlet 34 can accommodate a threaded connecting component or insert that interfaces with the threaded outlet 34 of the pump 14. This may include a connector (not shown) that is screwed into the internally threaded outlet 43. The threaded connecting component or insert may include any number of ends or connectors used in biopharmaceutical processes such as those described herein.

The outlet 43 is generally illustrated being oriented generally orthogonal to vertical axis of the flexible bag 12 (or substantially rigid container as explained below). It should be appreciated that the outlet 43 may exit the pump 14 at an angle. For example, the outlet 43 may be angled downward to facilitate easier usage. An angle (relative to horizontal) of about 15° to 45° would be common, although other angles are contemplated.

The pump 14, in one embodiment, operates as a diaphragm pump. A diaphragm pump operates by the actuation of multiple diaphragms 44 (FIGS. 2A and 2C) which are sequentially actuated to create a gentle pumping action of fluid through the pump. The diaphragms 44 work in conjunction with check-valves 46 to ensure the flow of fluid through the pump 14 in one direction. In one embodiment, actuation of the diaphragms 44 is effectuated by a nutating or wobble plate 48 (FIGS. 2B and 2C) that rotates about an axis to sequentially activate the diaphragms 44. As seen in FIGS. 2A-2C, a motor 50 is secured to the pump 14 and is coupled via a drive shaft (not shown) to the nutating disk or wobble plate 48 to actuate the multiple diaphragms 44 and pump fluid through the pump 14 from the inlet 42 to the outlet 43. Any number of types of motors 50 may be used including direct current motors, alternating current motors, and the like.

While there are four (4) diaphragms 44 illustrated in FIG. 2A, it should be understood that other configurations of the pump head 40 may contain fewer or more diaphragms 44. For example, additional diaphragms 44 may make for an even more smooth pumping action with reduced pulsatile flow effects. Likewise, while a motor 50 is illustrated as driving a nutating disk or wobble plate 48, an alternative construction of the pump 14 may utilize individual actuators (e.g., servo, electric, magnetic, or pneumatic) to sequentially actuate the diaphragms 44 to achieve the same pumping action without the need for a rotating disk or wobble plate 48. Thus, the motor 50 may be replaced with one or more servo actuators, electric/magnetic actuators or the like.

Figure 10:
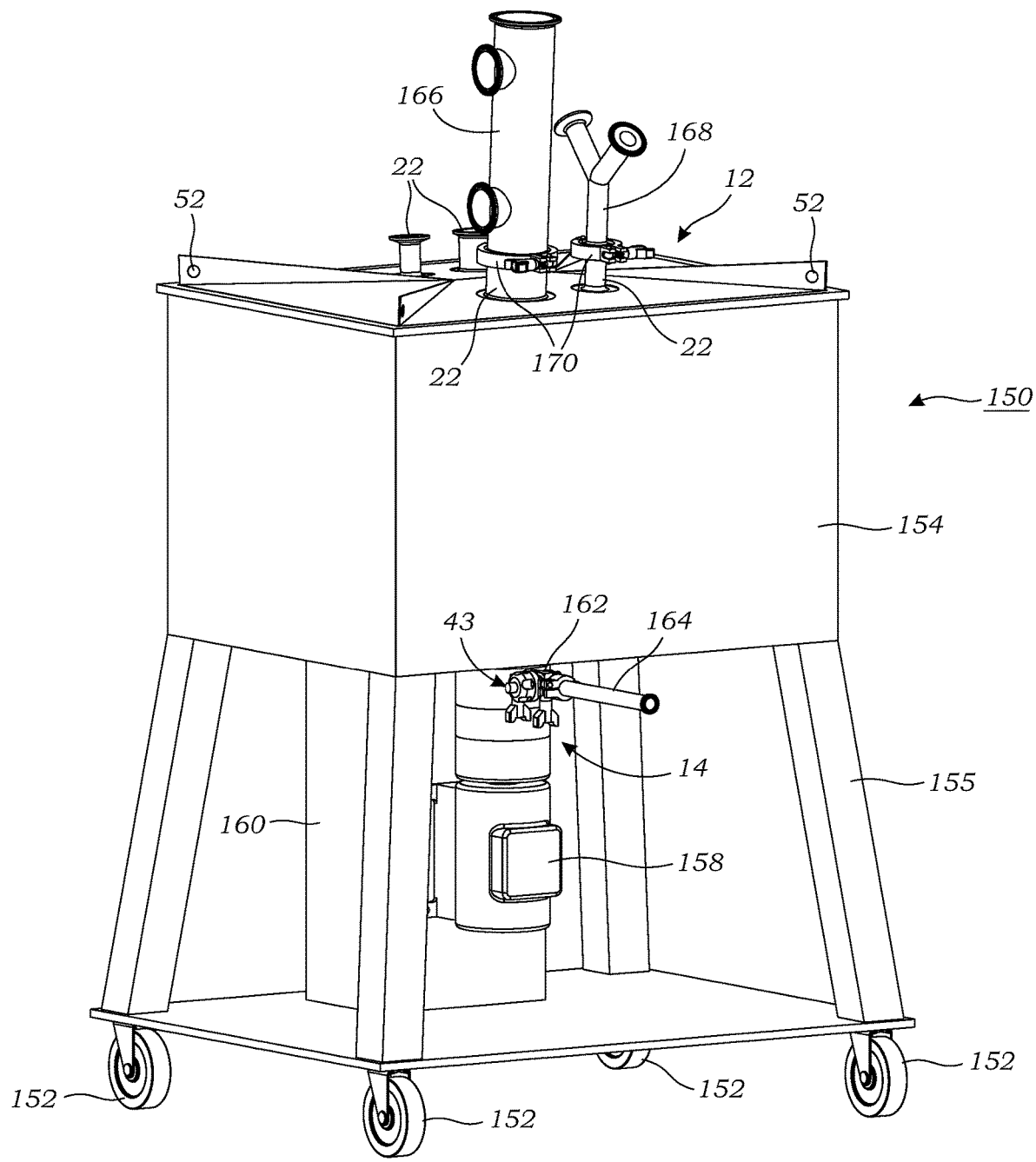
FIG. 10 illustrates one embodiment of a carrier in the form of a dolly or trolley that is used to hold a flexible bag with the integrated pump.

The flexible bag 12 may be housed in an outer support container 150 or the like such as that illustrated in FIG. 10 that holds the bags in the proper orientation during process operations (e.g., bottom surface 20 is held closest to ground so that surface of fluid moves from top to bottom as it is being pumped out of the flexible bag 12). These may be located on a cart, dolly, trolley, or the like so that fluids can be quickly connected/disconnected to process operations as needed. As seen in FIG. 2A, the flexible bag 12 may, in some embodiments, contain one or more optional hanging points 52 where the flexible bag 12 can be suspended from. Because of the weight of the pump 14 and the motor 50, the motor 50 may be secured to a support surface 160 or the like as is disclosed in FIG. 10 so as not put undue force on the flexible bag 12.

FIGS. 2A-2C illustrate an optional mixing adapter 60 that is used to at least partially cover the aperture 26 in the flexible bag 12 according to one embodiment. The mixing adapter 60 is used to ensure that materials such as powders or other solid media that may be added to the flexible bag 12 via a port 22 do not fall directly into the aperture 26 where the materials could interfere with the operation of the pump 14. The mixing adapter 60 also aids in mixing the fluid. In particular, as seen in FIG. 2C, the mixing adapter 60 includes a top curved surface in one embodiment that at least partially covers the cross-sectional area of the aperture 26 in the flexible bag 12. Fluid is able to enter the inlet 42 of the pump 14 around the sides of the mixing adapter. As seen in FIGS. 2B and 2C, the mixing adapter 60 may be secured to the pump head and projects centrally within the inlet 42 of the pump 14. The mixing adapter 60 may be made from any compatible materials including polymers and resins such as those described herein as well as metal (e.g., stainless steel).

Figure 3A:
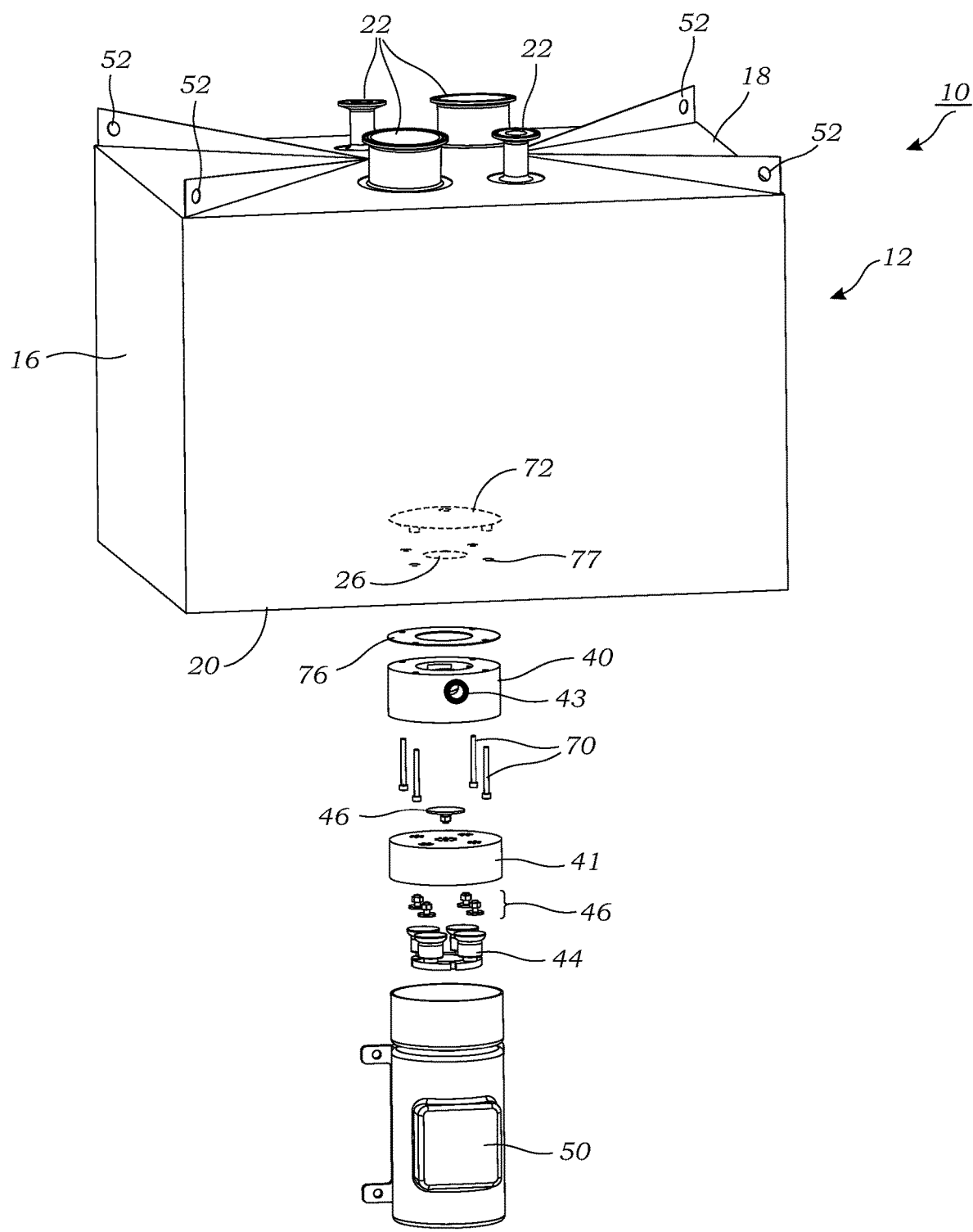
FIG. 3A illustrates an exploded view of a vessel in the form of a flexible bag that contains an integrated pump according to another embodiment.
Figure 3B:
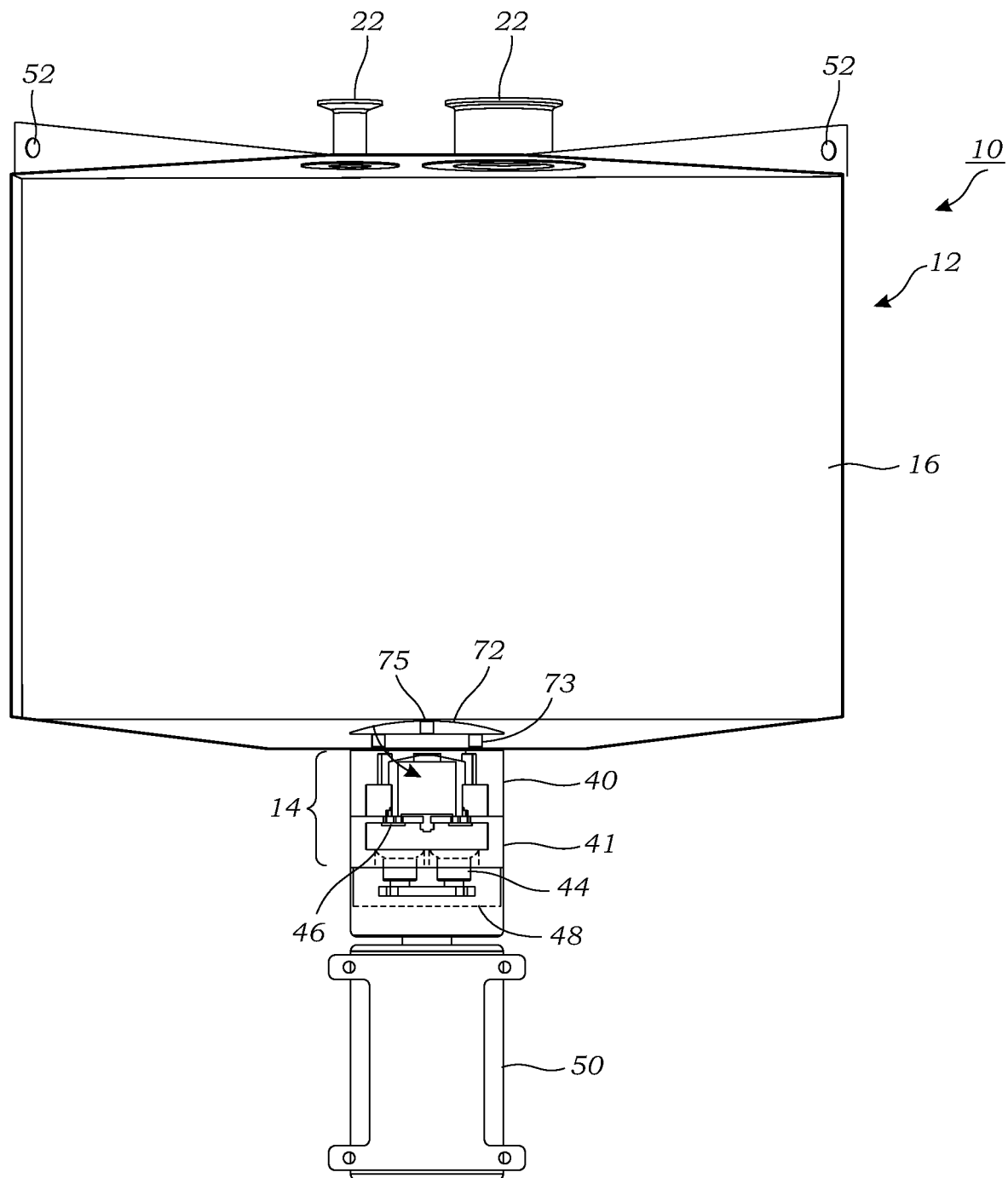
FIG. 3B illustrates a cross-sectional view of the flexible bag with integrated pump of FIG. 3A.
Figure 3C:
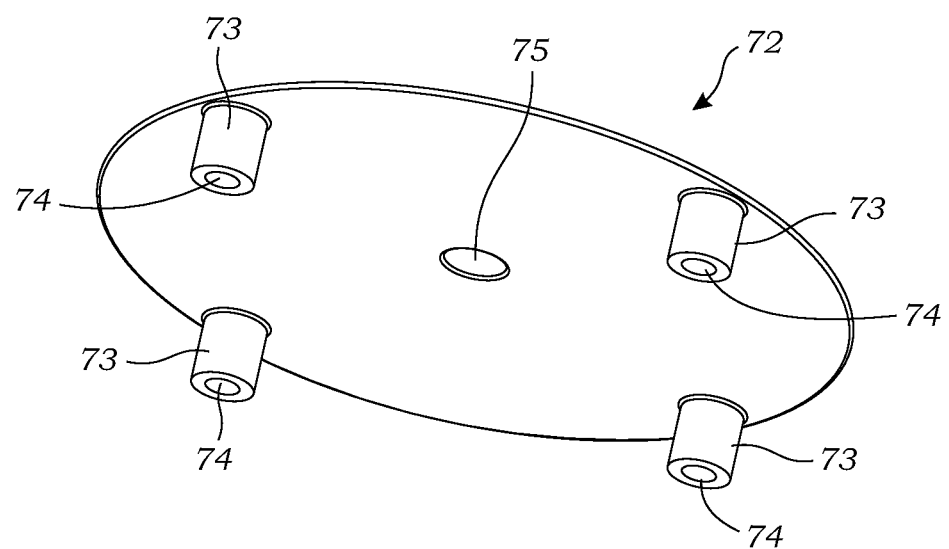
FIG. 3C illustrates a perspective view of the mixing adapter according to one embodiment.

FIGS. 3A-3C illustrate another embodiment of a vessel 10 in the form of a flexible bag 12 that contains an integrated pump 14. Similar elements to those of the embodiment of FIGS. 2A-2G will retain the same reference numbers for clarity. Unlike the embodiment of FIGS. 2A-2G, however, there is no separate port 28 that is placed in the aperture 26 of the flexible bag 12. In this embodiment, the pump head 40 of the pump 14 is secured to the flexible bag 12 using a plurality of fasteners 70 as seen in FIG. 3A that pass through corresponding holes or apertures in the bottom surface 20 of the flexible bag 12 and engage with mixing adapter 72. With reference to FIG. 3C, the mixing adapter 72 in the illustrated embodiment includes domed or curved top surface along with a plurality of standoffs 73 (e.g., legs, posts, boss) that contains apertures 74 therein for receiving the fasteners 70. The fasteners 70 may include screws (or bolts) that interface with corresponding holes or apertures 74 formed in the mixing adapter 72.

In this embodiment, the mixing adapter 72 also acts as a connection point for the pump 14. In this regard, the bottom surface 20 of the flexible bag 12 is interposed or pinched between the pump head 40 and the mixing adapter 72. The mixing adapter 72 may include one or more holes 75 in the surface thereof that allow the passage of fluid to the inlet 42 of the pump 14. Fluid also enters the inlet 42 of the pump 14 by entering along the gap formed between the bottom surface 20 of the flexible bag 12 and the mixing adapter 72. As seen in FIG. 3A, a circumferential gasket 76 is interposed between the pump head 40 and the bottom surface 20 of the flexible bag 12. On the interior of the flexible bag 12, individual gaskets 77 are interposed between the standoffs 73 of the mixing adapter 72 and the interior surface bottom surface 20 of the flexible bag 12 to provide a fluid-tight seal.

Figure 4A:
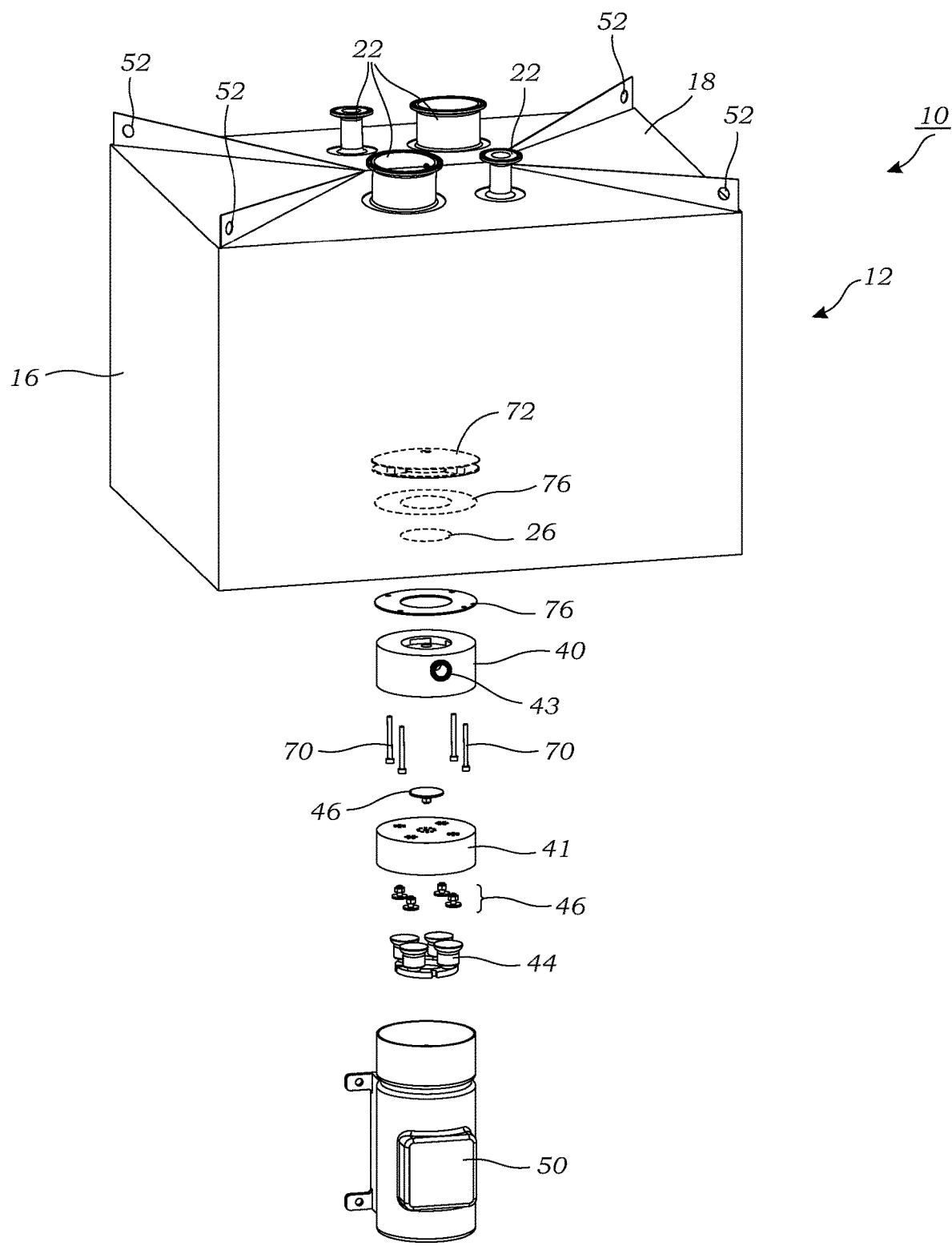
FIG. 4A illustrates an exploded view of a vessel in the form of a flexible bag that contains an integrated pump according to another embodiment.
Figure 4B:
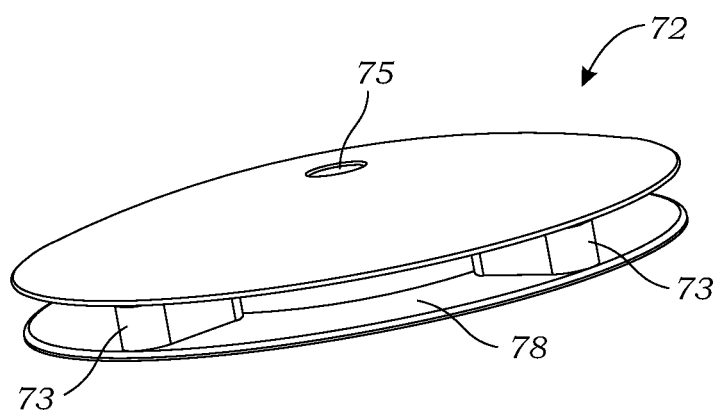
FIG. 4B illustrates a perspective view of the mixing adapter according to another embodiment.
Figure 4C:
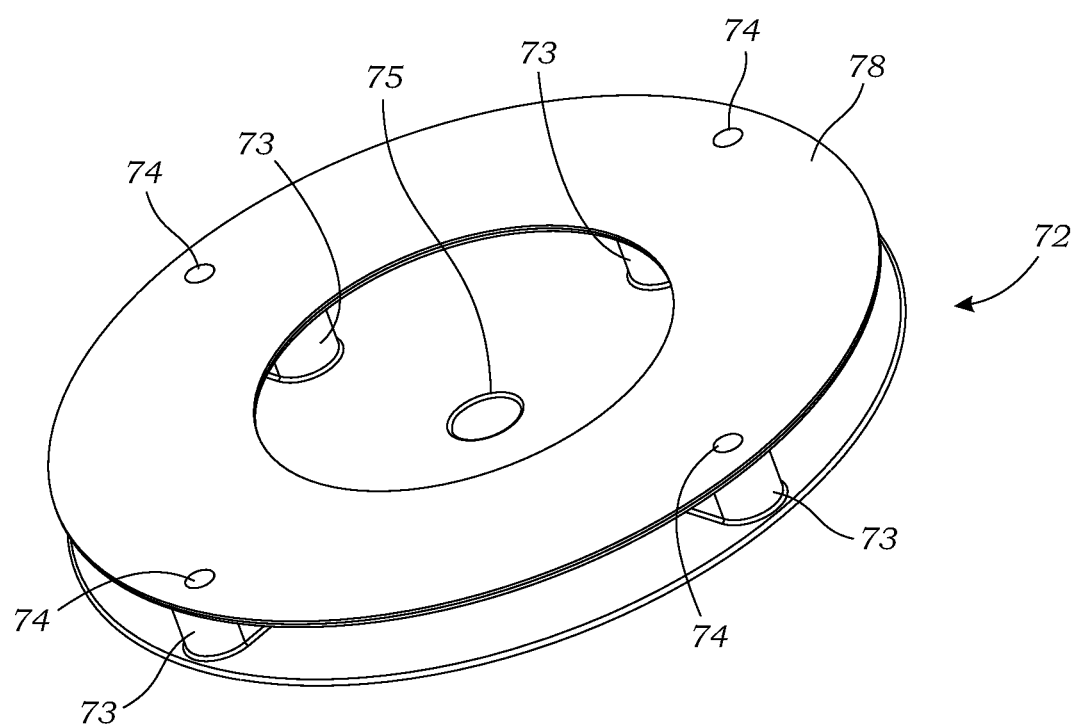
FIG. 4C illustrates another perspective view (showing underside) of the mixing adapter of FIG. 4B.

FIGS. 4A-4C illustrate another embodiment of a vessel 10 in the form of a flexible bag 12 that contains an integrated pump 14 that is modified from the embodiment of FIGS. 3A-3C. Again, similar elements to those of the embodiment of FIGS. 3A-3C will retain the same reference numbers for clarity. In this alternative embodiment, as best seen in FIGS. 4B and 4C, the mixing adapter 72 includes a lower circumferential flange 78 that is secured to the standoffs 73. The circumferential flange 78 mates with a corresponding circumferential gasket 76 that is interposed between the bottom surface 20 of the flexible bag 12 and the circumferential flange 78 when the fasteners 70 are used to secure the pump head 40 to the mixing adapter 72. In this embodiment, the separate gaskets 77 are omitted.

Figure 5A:
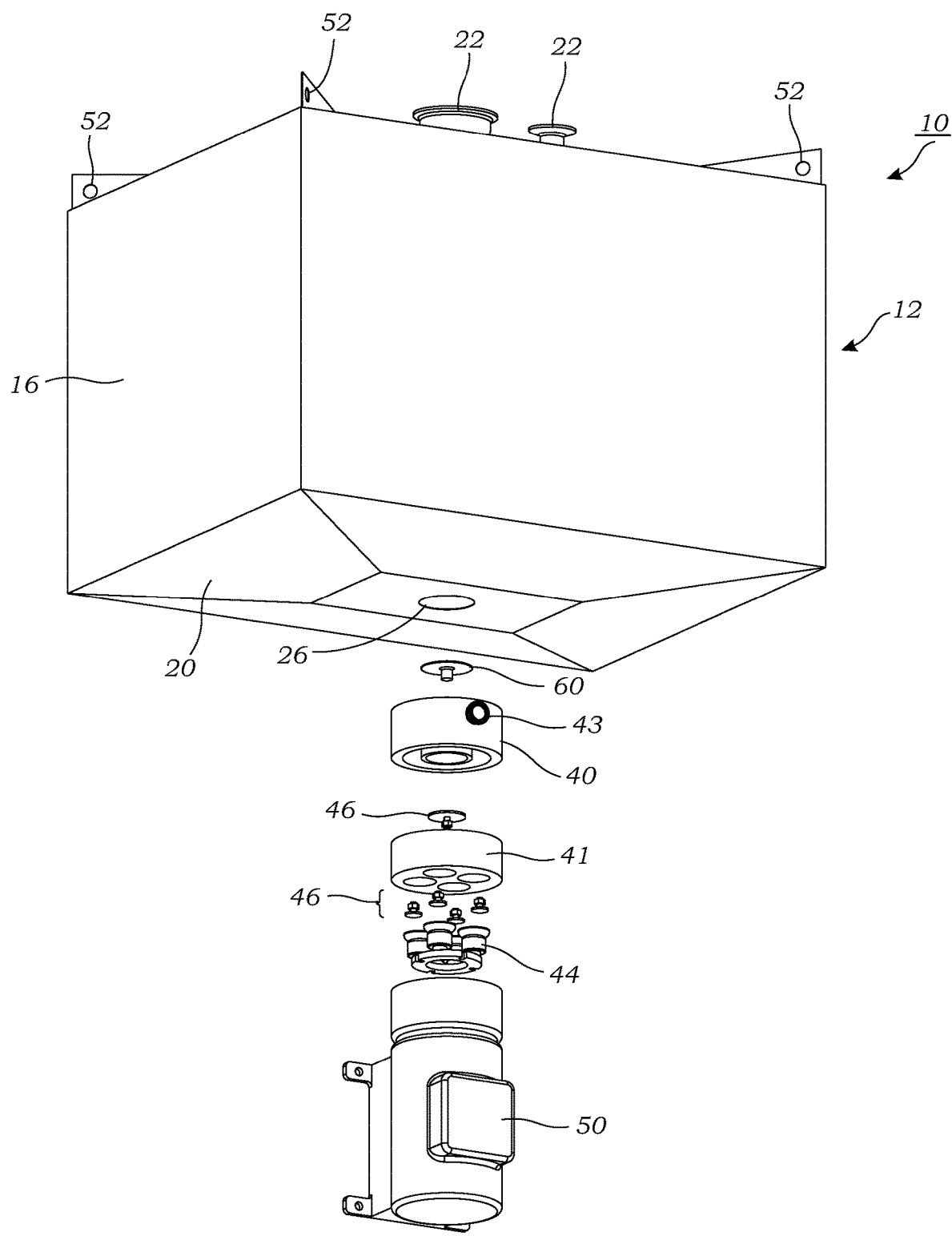
FIG. 5A illustrates an exploded view of a vessel in the form of a flexible bag that contains an integrated pump according to another embodiment.
Figure 5B:
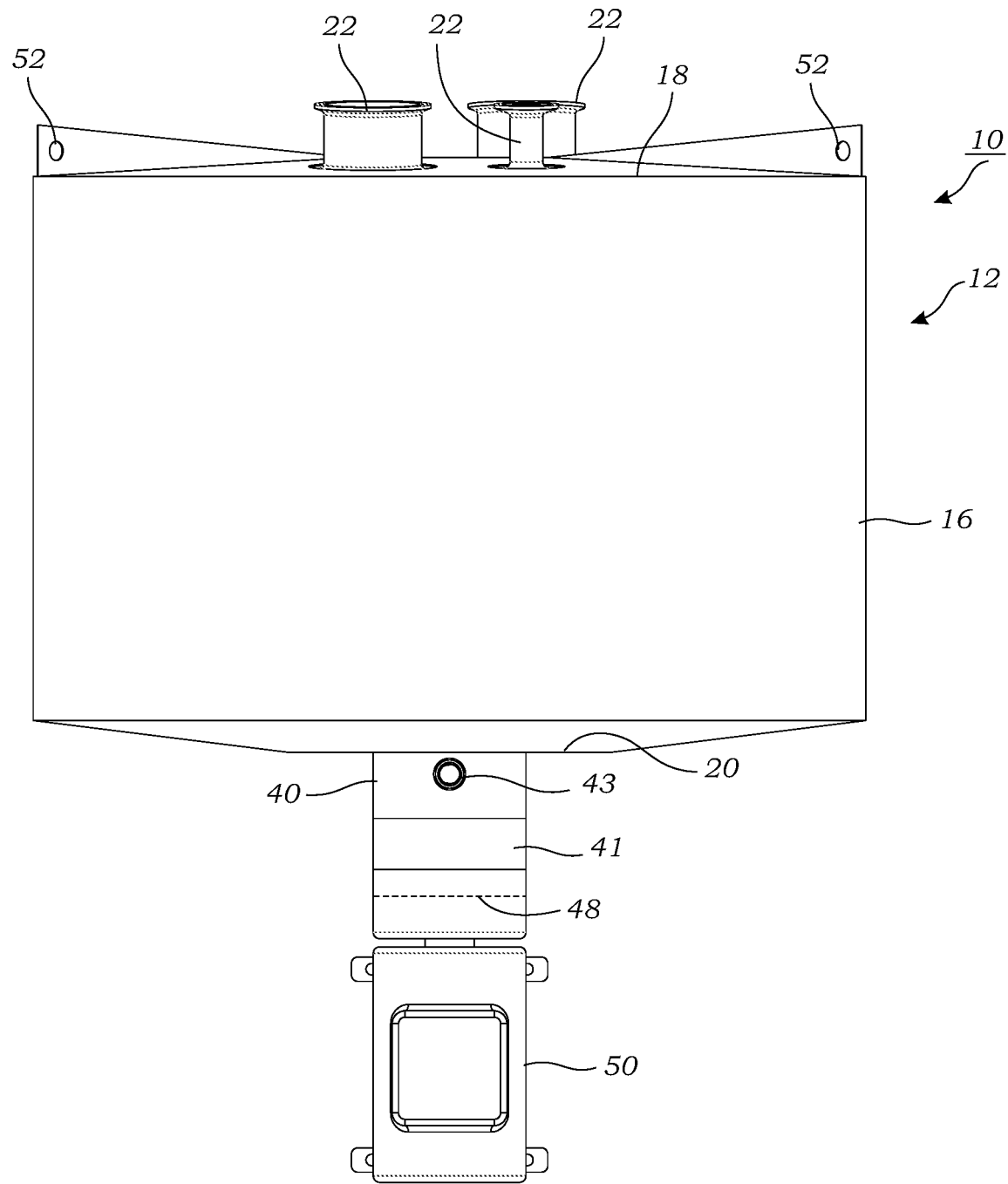
FIG. 5B illustrates a cross-sectional view of the flexible bag with integrated pump of FIG. 5A.

FIGS. 5A and 5B illustrate another embodiment of a vessel 10 in the form of a flexible bag 12 that contains an integrated pump 14. Similar elements to those of prior embodiments are illustrated with the same reference numbers for clarity. In this embodiment, the pump 14 is directly bonded to or integrally formed with the flexible bag 12. More specifically, the pump head 40 is directly bonded to the bottom surface 20 of the flexible bag 12. In this embodiment, the pump head 40 is secured to the flexible bag 12 by friction welding, ultrasonic welding, spin welding, laser welding, the use of an adhesive or glue, or other known bonding methods. The pump head 40 may also be integrally formed with the flexible bag 12 during the manufacturing of the pump head 40 and/or the flexible bag 12. In one embodiment, the pump head 40 may include a contact surface that contacts the flexible bag 12 that is formed from the same material used in the flexible bag 12. Alternatively, the pump head 40 may include a contact surface that contacts the flexible bag 12 that is a different material yet still provides a secure, fluid-tight bond. FIGS. 5A and 5B illustrate an optional mixing adapter 60 being used. It should be understood, however, that the pump 14 may still operate without the mixing adapter 60.

Figure 6A:
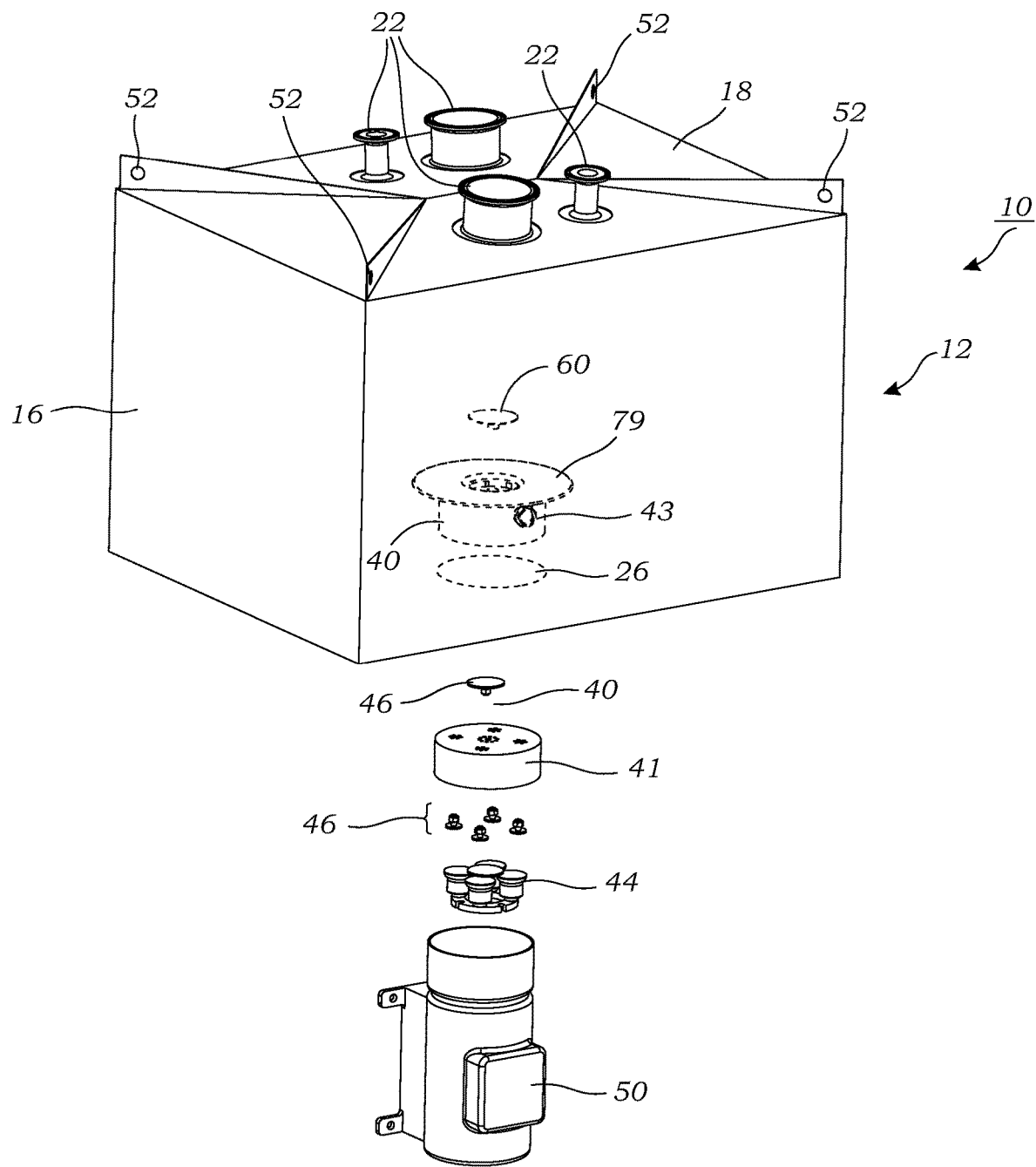
FIG. 6A illustrates an exploded view of a vessel in the form of a flexible bag that contains an integrated pump according to another embodiment.
Figure 6B:
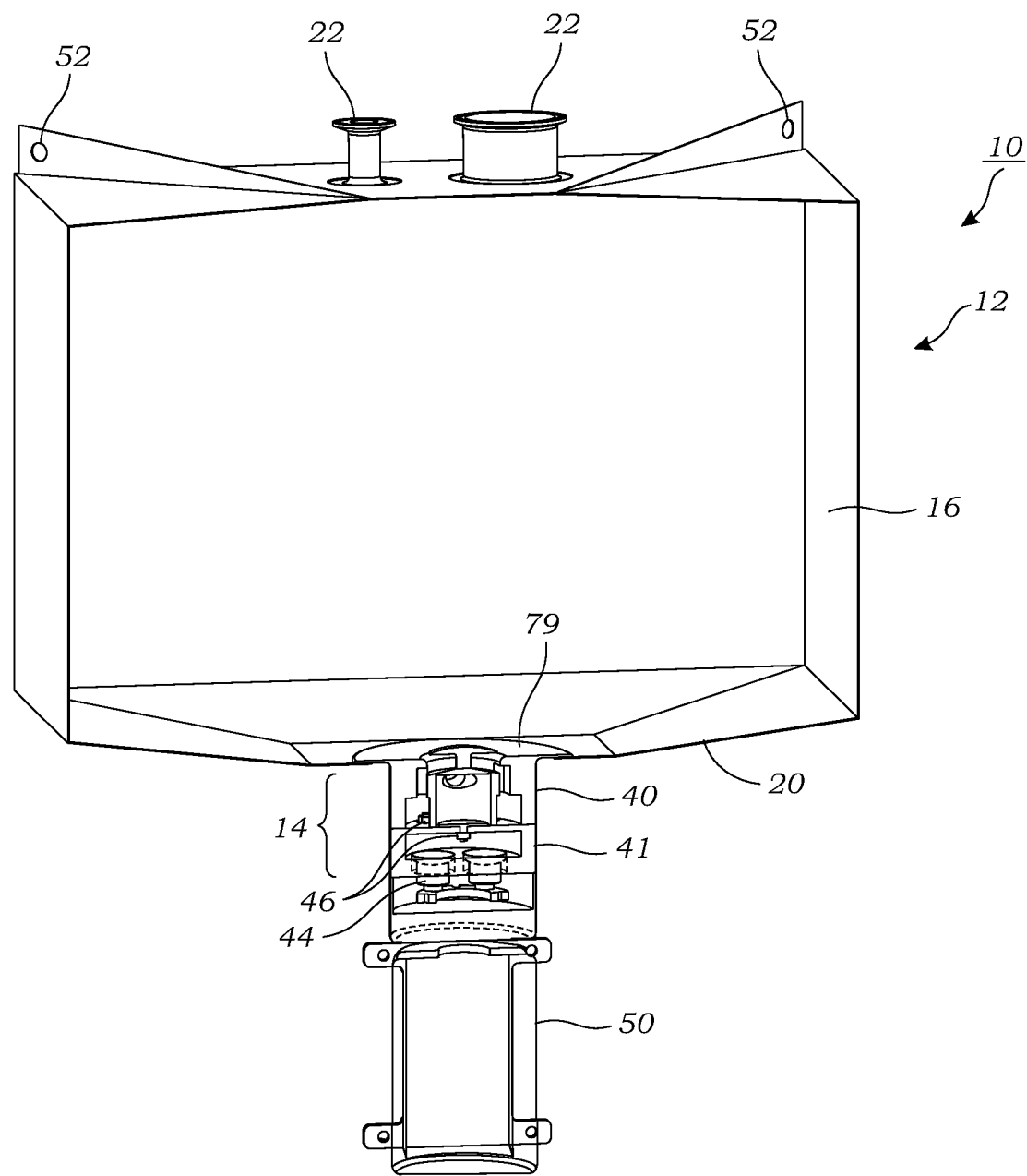
FIG. 6B illustrates a cross-sectional view of the flexible bag with integrated pump of FIG. 6A.
Figure 6C:
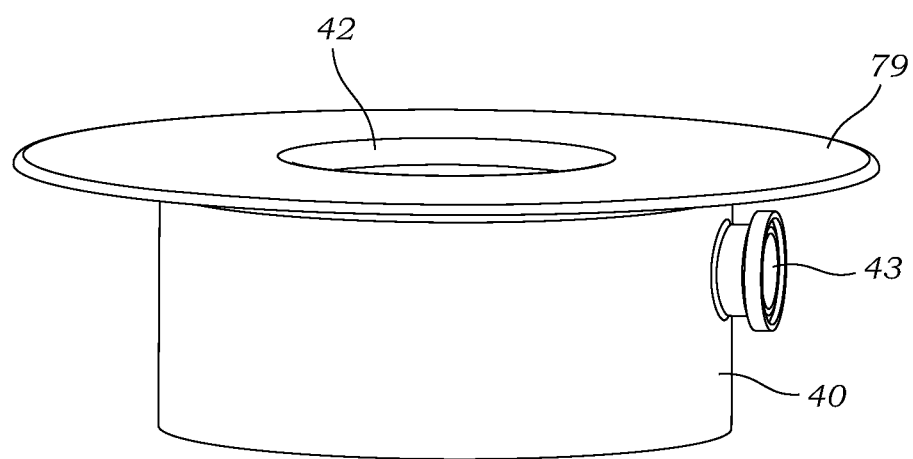
FIG. 6C illustrates a perspective view of a pump head used with the embodiment of FIG. 6B.

FIGS. 6A-6C illustrate another embodiment of a vessel 10 in the form of a flexible bag 12 that contains an integrated pump 14. Similar elements to those of prior embodiments are illustrated with the same reference numbers for clarity. In this embodiment, the pump 14 includes a flanged end 79 that is bonded, welded, or otherwise secured to the bottom surface 20 of the flexible bag 12. Specifically, the pump head 40 includes a flanged end 79 that extends radially outward and is bonded, welded, or otherwise secured to the inner or liquid-facing surface of the bottom surface 20 of the flexible bag 12. FIG. 6A illustrates an exploded view of the vessel 10 and components according to this embodiment. The pump head 40 includes a flanged end 79 at one end thereof that is bonded, welded, or otherwise secured to the flexible bag 12 as seen in FIG. 6B. As seen in FIG. 6A, the aperture 26 in the flexible bag 12 is larger to accommodate the pump head 40. FIG. 6C illustrates the pump head 40 having the flanged end 79 as well as the inlet 42 and outlet 43. While FIGS. 6A and 6B illustrate the flanged end 79 being bonded, welded, or otherwise secured to the inner (or liquid facing) of the bottom surface 20 of the flexible bag 12 it should be appreciated that the flanged end 79 may also be bonded, welded, or otherwise secured to the outer surface of the bottom surface 20 of the flexible bag 12.

Figure 7A:
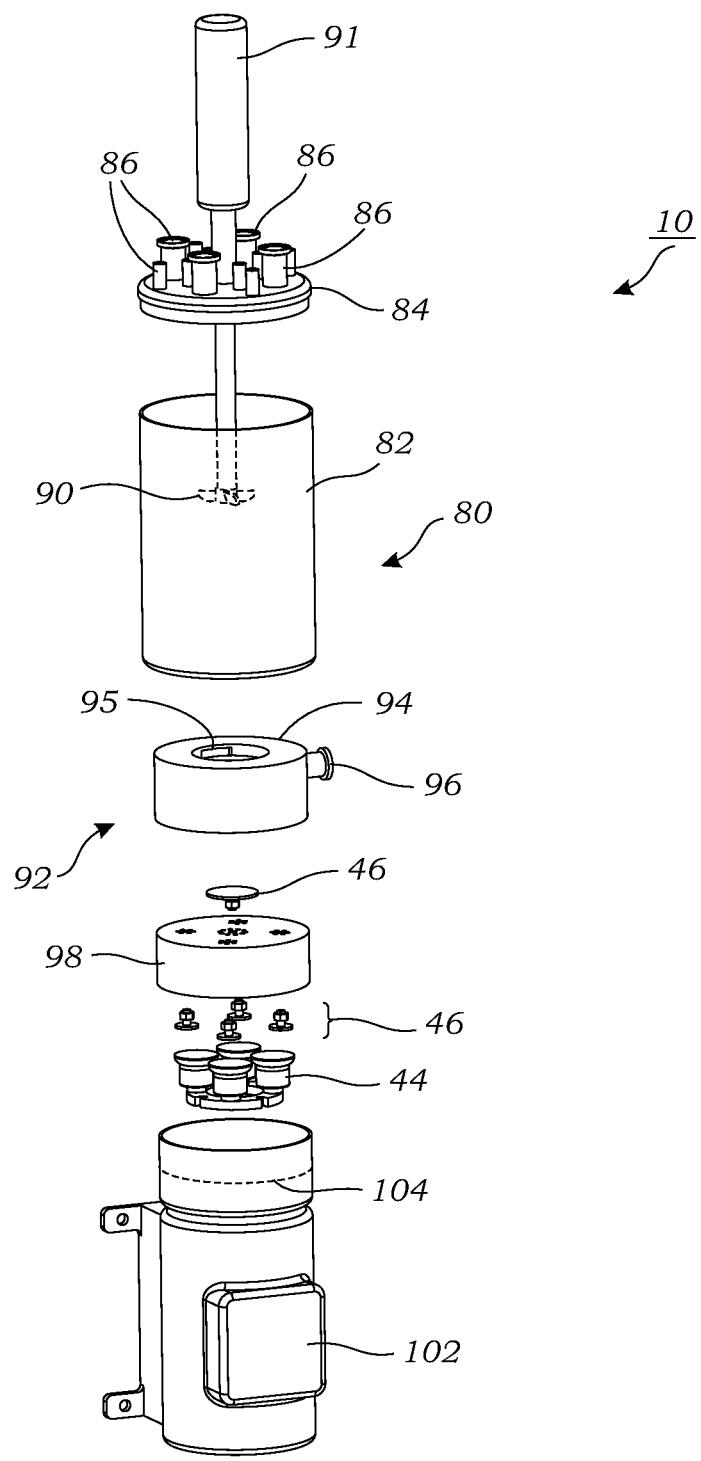
FIG. 7A illustrates an exploded view of a vessel in the form of a tank (e.g., bioreactor or fermenter) that contains an integrated pump according to another embodiment.
Figure 7B:
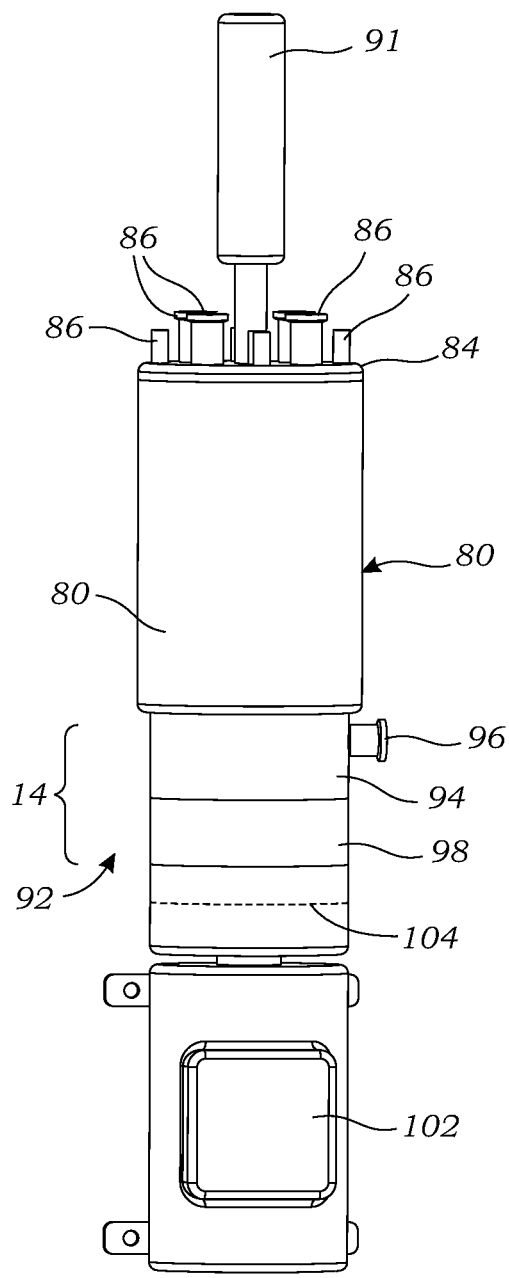
FIG. 7B illustrates a side view of the embodiment of FIG. 7A.

FIGS. 7A and 7B illustrate yet another embodiment of a vessel 10 in the form of a substantial rigid container 80 that includes a pump 14 (best seen in FIG. 7B) that is directly or indirectly secured to the substantially rigid container 80. The substantially rigid container 80 may include a tub, vat, barrel, bottle, tank, flask, or the like. The substantially rigid container 80 may be made, in one embodiment, in the form of a bioreactor or fermenter. The tank 82 includes one or more side surfaces and a bottom surface where the pump 14 is located. The tank 82 may be circular as illustrated and may have a wide variety of volumes. It should be understood that the tank 82 may have any number of geometric shapes and sizes. Typically, the height of the tank 82 is at least 1.5 times the diameter of the tank 82 but other sizes are contemplated. In one embodiment, the substantial rigid container 80 includes a liquid-containing tank 82 and a lid 84 that contains optional ports 86. These ports 86 may provide access to add or remove fluid containing the tank 82. The ports 86 may also hold or contain sensors or probes that are used to monitor the conditions inside the tank 82. The ports 86 may also provide access to mixers, gas introducers, agitators, gas bubblers, and the like. The ports 86, in some embodiments, may terminate in a variety of ends or connectors used in biopharmaceutical processes. These include hygienic connectors, hose barbs, flanges, TC connectors, disposable aseptic connectors (DAC), and the like. While the ports 86 are illustrated in the lid 84 they may also be incorporated into the tank 82 itself (e.g., on the sidewalls) in some alternative embodiments. For example, a port 86 may be located at a side of the tank 82 near the bottom to provide access for a mixer device or the like.

The tank 82 and lid 84 may be made from a polymer, plastic material, or resin that mimics the performance of glass or stainless steel. The polymer material preferably complies with Class IV standards or higher levels of biocompatibility and chemical resistance as needed, and is free of or contains low amounts of leachable and extractable material. Examples of polymers that can be used to form the substantially rigid container 80 include polyethylene, polycarbonate, and as well as the materials noted above with respect to the flexible bag 12 embodiment. Medical-grade resins compliant with class VI standards may also be used. Alternatively, the tank 82 and/or lid 84 may be made from a metal such as stainless steel. The tank 82 and/or lid 84 may also be made of glass. In some embodiments, the vessel 10 is designed as a single-use vessel 10 that is discarded after a batch or continuous run of products has completed. In other embodiments, the vessel 10 may be designed to be sterilized and reused.

Figure 8A:
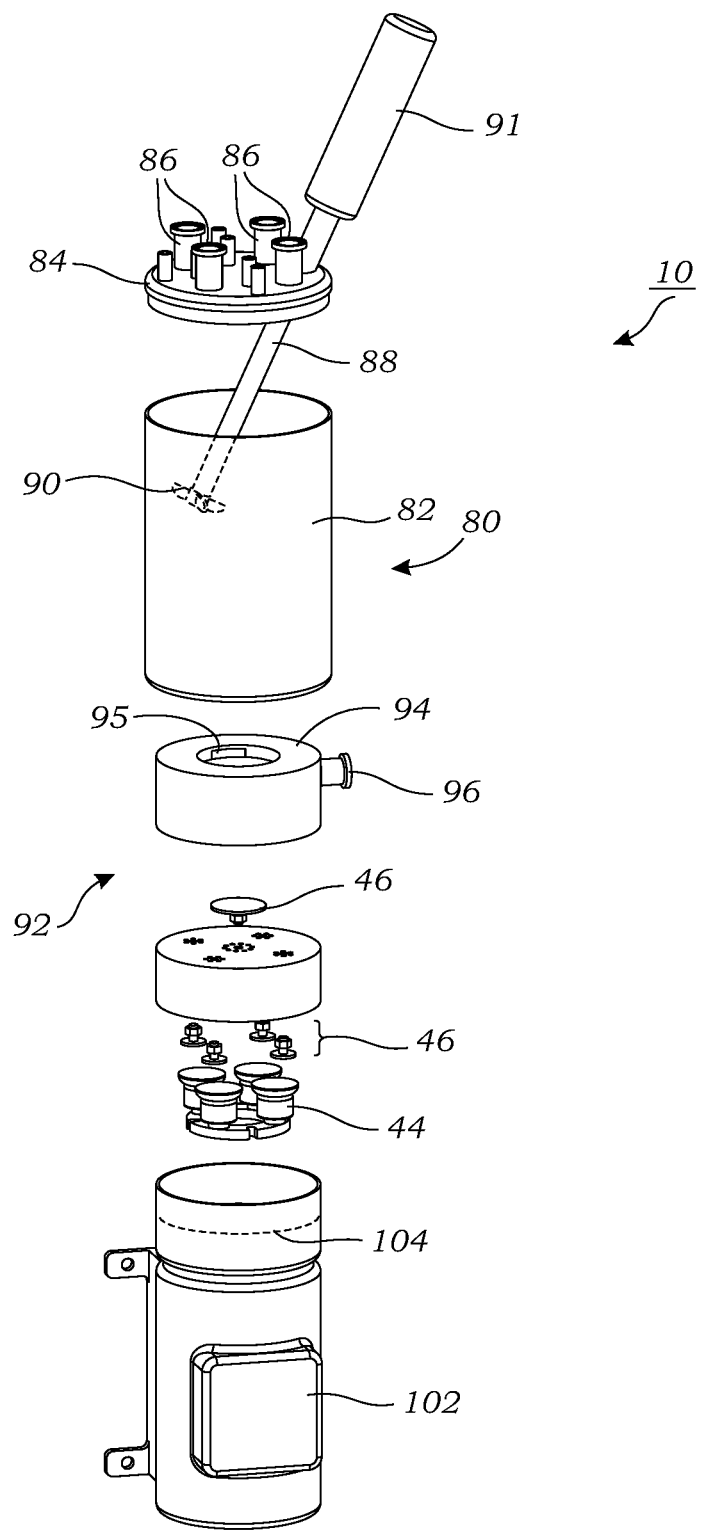
FIG. 8A illustrates an exploded view of a vessel in the form of a tank (e.g., bioreactor or fermenter) that contains an integrated pump according to another embodiment.
Figure 8B:
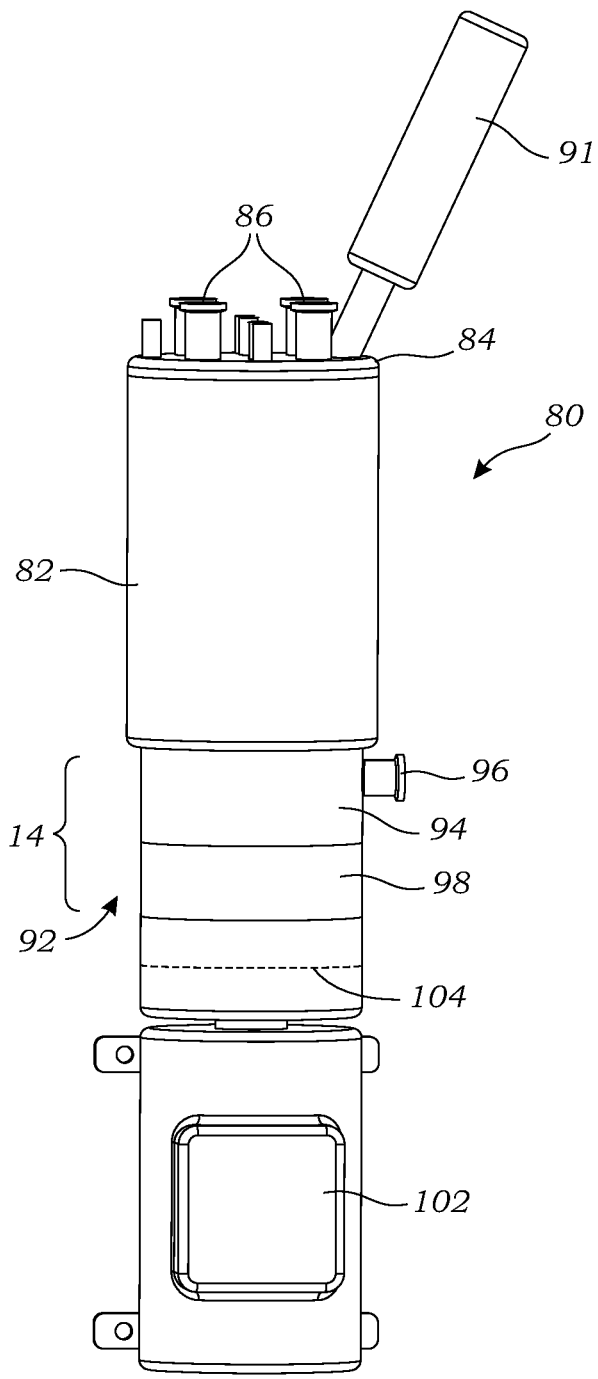
FIG. 8B illustrates a side view of the embodiment of FIG. 8A.

In some embodiments, as best seen in FIG. 7A, the liquid-containing tank 82 includes a shaft 88 that extends longitudinally along the length of the tank 82 and has mounted thereon an impeller 90. The rotating shaft 88 and impeller 90 are used to mix fluid contained in the tank 82. The shaft 88 may be coupled to a motor 91 to rotate the shaft 88 and impeller 90 at the desired rotational speeds. FIGS. 8A and 8B illustrates an alternative embodiment of the substantial rigid container 80 (e.g., tank 82 and lid 84) that employs an angled mixer that is formed by an angled shaft 88 that includes an impeller 90 mounted thereon. The angled shaft 88 passes through lid 84 where it interfaces with the motor 91.

As seen in FIGS. 7B and 8B, a pump 14 is secured to the bottom surface of the tank 82. The bottom surface may a flat bottom surface of the tank 82 or it may include a rim (e.g., circumferential rim) defined by the wall(s) of the tank 82. For example, as explained herein, the pump head 92 may form at least part of the bottom surface of the tank 82. In one embodiment, as seen in FIGS. 7A and 8A, the pump 14 includes a pump head 92 or a portion of the pump head 92 that is integrated into the tank 82. For example, the tank pump 92 or portion thereof may be integrally formed with the tank 82. This may occur during the molding operation in which the pump head 92 is integrally manufactured along with the tank 82 (e.g., a unibody construction). Alternatively, the pump head 92 may be secured to the tank 82 by friction welding, ultrasonic welding, spin welding, laser welding, the use of an adhesive or glue, or other known bonding methods. For example, the pump head 92 or a portion thereon (e.g., upper portion 94 described below). In yet another alternative, the pump head 92 may be secured to the tank 82 using one or more fasteners similar to the embodiment of FIG. 3A-3C or 4A-4C. In yet another alternative, the pump head 92 may be secured to the tank 82 using a port such as port 24 of FIG. 2F.

As seen in FIGS. 7A and 8A, the pump head 92 includes an upper head portion 94 that contains the fluid outlet 96 which is integrally formed with the tank 82. The pump head 92 includes a lower portion 98 that contains the pumping mechanism, which in the illustrated embodiment is a diaphragm pump as previously explained, although other pump types may be used. For example, the pump head 92 may operate as a centrifugal pump. In some embodiments, the pump head 92 may be formed as a single or unitary piece instead of the two-piece construction as illustrated. Likewise, in still other embodiments, the pump head 92 may have more than the upper and lower portions 94, 98.

The integral formation with the tank 82 may occur during the manufacturing process or the pump head 92 (e.g., one or more of upper portion 94 or lower portion 98) may be bonded together using one or more of the bonding techniques described herein (e.g., thermal bonding, an adhesive, glue, weld, or the like). Thus, in some embodiments, the pump head 92 or portions thereof such as the upper portion 94 and/or lower portion 98 may be made from the same polymer or resin material that is used to form the tank 82. In other embodiments, the pump head 92 or portions thereof may be formed from different materials that are still compatible with bonding to the tank 82. The portion of the pump head 92 that is bonded, welded, adhered, or integrated with the tank 82 (e.g., the upper head portion 94) should, in one embodiment, preferably made from plastic or resin materials that are also compatible with the bioprocess or chemical process taking place inside the vessel 10. The upper portion 94 of the pump head 92 includes a pump inlet 95 that is open to and communicates with the interior of the tank 82. The bottom of the tank 82 may include an opening like aperture 26 in the flexible bag 12 embodiment or the bottom of the tank 82 may be completely open and sealed off when the pump head 92 is secured thereto. Advantageously, there are no intermediate conduits or lines between the pump inlet 95 and the tank 82 as the pump 14 is connected to the substantial rigid container 80.

As seen in FIGS. 7A and 8A, the pump head 92 includes a lower head portion 98 that contains the pumping mechanism or drive components. In one preferred embodiment, the lower head portion 98 contains the diaphragm pump components as described previously. This includes the multiple diaphragms 44 and check-valves 46 which are sequentially actuated as previously explained herein to create a gentle pumping action of fluid through the pump 14. In the embodiment of FIGS. 7A, 7B, 8A, 8B, a motor 102 is secured to the lower head portion 98 using a plurality of fasteners or the like. The motor 102 is used to sequentially actuate the diaphragms 44 to pump fluid from the tank 82 to the outlet 96. In one embodiment, actuation of the diaphragms 44 is effectuated by a nutating or wobble plate 104 (FIGS. 7A, 7B, 8A and 8B) that rotates about an axis to sequentially activate the diaphragms 44. While a motor 102 is illustrated as driving a nutating disk or wobble plate 104, an alternative construction of the pump 14 may utilize individual actuators (e.g., servo or pneumatic) to sequentially actuate the diaphragms 44 to achieve the same pumping action without the need for a rotating disk or wobble plate 104.

The outlet 96 of the pump 14 may terminate in a variety of ends or connectors used in biopharmaceutical processes. These include hygienic connectors, hose barbs, flanges, TC connectors, disposable aseptic connectors (DAC), and the like. In this embodiment, the motor 102 may include a mounting plate 104 that can be mounted on a sturdy surface so that the tank 82 may be held in a substantially upright orientation. The substantial rigid container 80 of the embodiment illustrated in FIGS. 7A, 7B, 8A, and 8B may contain an optional mixing adapter 60 like that illustrated in FIGS. 2A, 2B, 2C, 5A or mixing adapter 72 illustrated in FIGS. 3A, 3B, 3C, 4A, 4B, 4C that is used to at least partially cover the inlet 95 of the pump 14.

The outlet 96 may include or incorporate a valve directly or indirectly in the outlet 96. Tubing or other conduit may also interface directly with the outlet 96 of the pump 14 (e.g., by welding to the outlet 96 or the like). In still another embodiment, the outlet 96 of the pump 14 may simply be an aperture or opening through which fluid passes. This aperture or opening may be threaded internally so that the outlet 96 can accommodate a threaded connecting component or insert that interfaces with the threaded outlet 96 of the pump 14. This may include a connector (not shown) that is screwed into the internally threaded outlet 96. The threaded connecting component or insert may include any number of ends or connectors used in biopharmaceutical processes such as those described herein.

Figure 9:
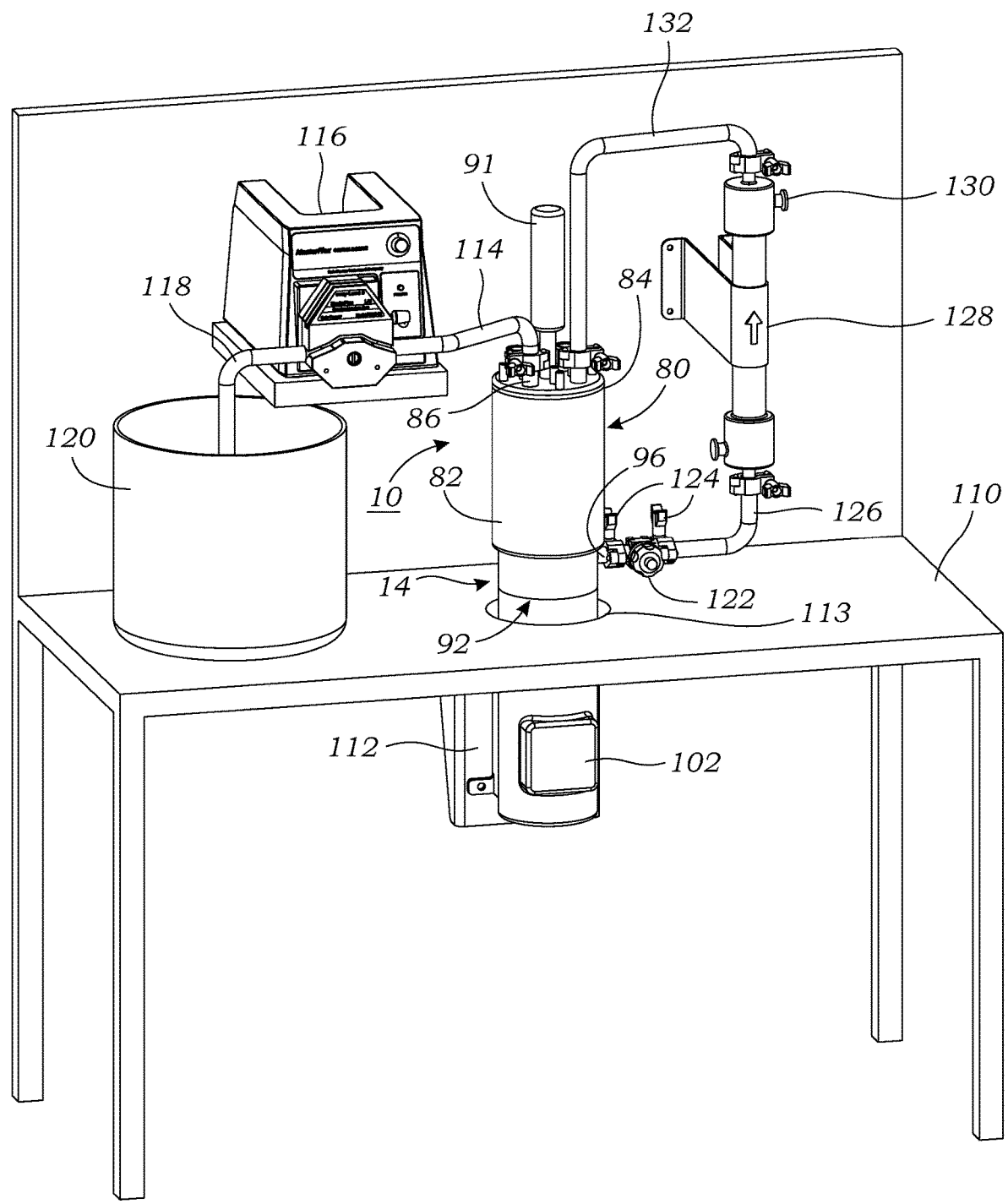
FIG. 9 illustrates one embodiment of the vessel used as a perfusion bioreactor and mounted on a table or support.

FIG. 9 illustrates one embodiment of the vessel 10 in the form of a substantial rigid container 80 of FIGS. 7A, 7B, 8A, 8B being used as a bioreactor. A table or other support 110 is provided for holding the various components in place. In this embodiment, the pump 14 is illustrated on the bottom of the tank 82 and the tank 82 is held in a vertical orientation by the motor 102 that is mounted vertically to the table or support 110 using support 112. The motor 102 and/or pump 14 passes through an aperture 113 formed in the table or support 110. As seen in FIG. 9, one of the ports 86 in the cover 84 is connected to a conduit 114 that leads to a peristaltic pump 116. The peristaltic pump 116 is coupled via another conduit 118 that leads to a tank 120 that, in one embodiment, holds fresh medium that is to be delivered to the tank 82. In this regard, the peristaltic pump 116 is used to pump fresh fluid medium into the tank 82. The outlet 96 of the pump head 92 is connected to a diaphragm valve 122 via clamps 124. The outlet of the diaphragm valve 122 is connected to a conduit 126 that leads to a filtration or separation unit 128. In the embodiment illustrated n FIG. 9, this is a hollow fiber filter module 128. For example, this may be a hollow fiber tangential flow filter cartridge which are commercially available. The filtration or separation unit 128 may be any type of filter or separation unit. These include conventional tangential flow filtration units, acoustic separators, and the like. The filtration or separation unit 128 is used to filter out desired end products (e.g., drugs) or waste products via outlet port 130 while the non-filtered cells can be returned back to the tank 82 via conduit 132. It should be appreciated that the particular arrangement illustrated in FIG. 9 is illustrative and the vessels 10 described herein (including the flexible bag 12 and the rigid container 80) may be used in any number of configurations depending on the application in which they are used.

The conduits 114, 118, 126, 132 of FIG. 9 may be made of any number of biocompatible materials including metals or polymers as silicone which may be either reinforced or un-reinforced. In one particular embodiment, the conduits 114, 118, 126, 132 are formed from an un-reinforced polymer such as silicone and surrounding by sections or segments of interconnected rigid, external jackets such as those disclosed in International Patent Publication No. WO 2016/100396 A1; also U.S. patent application Ser. No. 15/535,601, which are incorporated by reference herein.

FIG. 10 illustrates one embodiment of a carrier 150 in the form of a dolly or trolley that is used to hold a flexible bag 12 with the integrated pump 14. The carrier 150 may be mobile or fixed. FIG. 10 illustrates a mobile carrier 150 that uses a plurality of wheels 152 so that the carrier 150 may be moved. The flexible bag 12 is contained within a bin 154 supported by a frame 155 that is dimensioned to hold or accommodate the size of the flexible bag 12. The carrier 150 is formed from a sturdy material such as metal or plastic so that it can accommodate the weight of the fluid contained in the flexible bag 12 and the integrated pump 14. As seen in FIG. 10, the bin 154 includes an aperture formed in the bottom surface so that the pump 14 and attached motor 158 are located external to and beneath the bin 154. The motor 158 may mounted to a support 160 that is integrated in the frame 155 of the carrier 150. The support 160 ensures that the pump 14 and motor 158 are generally oriented in the vertical direction and so that the weight of the pump 14 and motor 158 do not pull on the flexible bag 12.

FIG. 10 illustrates the pump outlet 43 connected to a diaphragm replacement valve 162 that is connected to a conduit 164. For example, this may include a diaphragm replacement valve (DRV) sold by Aquasyn LLC, Carson City, Nev. The ports 22 on the flexible bag 12 are also illustrated, in this particular depiction, being connected to a various conduits, tubing, or connectors 166, 168. These may be connected to the ports 22 using, for example, clamps 170. The types of conduits 164, tubing, and connectors 166, 168 may vary depending on the particular application in which the flexible bag 12 is used. The conduits 164, tubing, and connectors 166, 168 may be formed from a rigid material such as a metal (e.g., stainless steel) or they may be formed from a polymer material. For example, the conduit 164 or tubing may be formed from silicone or the like for single-use applications. In one particular embodiment, flexible bag 12, the pump 14, It should be appreciated that while the embodiments of the pump 14 described herein are described in the context of a diaphragm pump, the invention is not limited to diaphragm pumps. Other pumps may also be used. These include by way of illustration, centrifugal pumps, or other positive displacement pumps. For example, if mammalian cells are not used in the flexible bag 12, the gentle pumping action of the diaphragm pump may not be needed in which case other pumps such as a centrifugal pump may be used. Such pumps would be integrated into or connected to the flexible bag 12 or the tank 82 using a similar pump head as described herein, albeit one operates using a different pumping mechanism. In addition, while the embodiments of the vessels 10 with an integrated pump 14 have been described as using a conventional rotary motor to power the pump 14, in other embodiments a different type of pump driver can be employed to pump fluid from the vessel 10. For example, for a diaphragm pump 14, the diaphragms 44 may be actuated in the desired sequence and speed using servos associated with each diaphragm 44 to generate the same pumping action.

While embodiments of the present invention have been shown and described, various modifications may be made without departing from the scope of the present invention. Moreover, it should be appreciated that aspects of one embodiment may be utilized in other embodiments described herein. Thus, feature of one embodiment may be substituted or used in other embodiments. This includes, by way example, the mixing adaptors, ports, pumps, pump connection types, motors, and the like. In addition, while the embodiments described herein have largely been described being used in the context of a bioprocess or pharmaceutical operation, the embodiments are not limited to those applications. For example, the concepts and embodiments described herein may be applied to high purity chemical systems or in other industries. The invention, therefore, should not be limited except to the following claims and their equivalents.

What is claimed is:

1. A bioprocess vessel having an integrated pump comprising:
    a flexible bag defining an interior volume and having a bottom surface, the bottom surface containing an aperture therein for the passage of fluid;

a port disposed in the aperture and secured to the bottom surface of the flexible bag; and a pump head and having an inlet and an outlet, the pump head having a flanged end that is secured to the port and further including a plurality of diaphragms, each diaphragm associated with a check-valve, wherein sequential actuation of the plurality of diaphragms pumps fluid from the interior volume of the flexible bag into the inlet and out of the outlet.

2. The bioprocess vessel of claim 1, wherein the port comprises a flanged end and wherein the flanged end of the pump head is secured to the flanged end of the port.

3. The bioprocess vessel of claim 1, further comprising a mixing adapter secured to the pump head and disposed at least partially in the interior volume of the flexible bag, the mixing adapter at least partially covering the inlet of the pump head.

4. The bioprocess vessel of claim 1, the pump head further comprising a nutating disk or wobble plate configured to sequentially actuate the plurality of diaphragms.

5. The bioprocess vessel of claim 4, further comprising a detachable motor secured to the pump head.

6. The bioprocess vessel of claim 1, further comprising a plurality of actuators configured to sequentially actuate the plurality of diaphragms.

7. A bioprocess vessel having an integrated pump comprising:
a substantially rigid container formed from a resin or polymer material defining an interior volume and having a bottom surface; and
a port disposed in the bottom surface of the substantially rigid container; and
a pump head and having an inlet and an outlet, the pump head having a flanged end that is secured to the port and further including a plurality of diaphragms, each diaphragm associated with a check-valve, wherein sequential actuation of the plurality of diaphragms pumps fluid from the interior volume of the substantially rigid container into the inlet and out of the outlet.

8. The bioprocess vessel of claim 7, wherein the port comprises a flanged end and wherein the flanged end of the pump head is secured to the flanged end of the port.

9. The bioprocess vessel of claim 7, further comprising a mixing adapter secured to the pump head and disposed at least partially in the interior volume of the substantially rigid container, the mixing adapter at least partially covering the inlet of the pump head.

10. The bioprocess vessel of claim 7, the pump head further comprising a nutating disk or wobble plate configured to sequentially actuate the plurality of diaphragms.

11. The bioprocess vessel having an integrated pump of claim 10, further comprising a detachable motor secured to the pump head.

12. The bioprocess vessel of claim 7, further comprising a plurality of actuators configured to sequentially actuate the plurality of diaphragms.

13. The bioprocess vessel of claim 7, further comprising a lid having one or more ports formed therein.

14. The bioprocess vessel of claim 13, further comprising a rotating shaft extending through the lid and into the interior of the substantially rigid container and having an impeller thereon.

* * * * *